(12) United States Patent
Pfeifer et al.

(10) Patent No.: US 11,684,576 B2
(45) Date of Patent: Jun. 27, 2023

(54) METHOD OF SAFE ADMINISTRATION OF PHOSPHORYLATED TAU PEPTIDE VACCINE

(71) Applicants: AC Immune SA, Lausanne (CH); Janssen Pharmaceuticals, Inc., Titusville, NJ (US)

(72) Inventors: Andrea Pfeifer, St. Legier (CH); Andreas Muhs, Cugy (CH); Maria Pihlgren Bosch, Mont-sur-Lausanne (CH); Marija Vukicevic Verhille, St-Sulpice (CH); Nicolas Piot, Grandvaux (CH); Saroj Raj Ghimire, Chavannes-pres-Renens (CH); Elizabeth Anne Ramsburg, Chalfont, PA (US); Donata De Marco, Turnhout (BE); Charlotte Sadaka, San Diego, CA (US)

(73) Assignees: AC Immune SA, Lausanne (CH); Janssen Pharmaceuticals, Inc., Titusville, NJ (US)

( * ) Notice: Subject to any disclaimer, the term of this patent is extended or adjusted under 35 U.S.C. 154(b) by 285 days.

(21) Appl. No.: 16/785,011

(22) Filed: Feb. 7, 2020

(65) Prior Publication Data
US 2020/0253873 A1     Aug. 13, 2020

Related U.S. Application Data

(60) Provisional application No. 62/802,870, filed on Feb. 8, 2019.

(51) Int. Cl.
| A61K 9/127 | (2006.01) |
| A61P 25/28 | (2006.01) |
| A61K 39/00 | (2006.01) |

(52) U.S. Cl.
CPC ........ *A61K 9/1271* (2013.01); *A61K 39/0007* (2013.01); *A61P 25/28* (2018.01);
(Continued)

(58) Field of Classification Search
None
See application file for complete search history.

(56) References Cited

U.S. PATENT DOCUMENTS

| 5,843,779 A | 12/1998 | Vandermeeren et al. |
| 7,408,027 B1 | 8/2008 | Mandelkow et al. |
| (Continued) | | |

FOREIGN PATENT DOCUMENTS

| EP | 2210901 A1 | 7/2010 |
| WO | 9014837 A1 | 12/1990 |
| (Continued) | | |

OTHER PUBLICATIONS

Kwong B, Liu H, Irvine DJ. Induction of potent anti-tumor responses while eliminating systemic side effects via liposome-anchored combinatorial immunotherapy. Biomaterials. Aug. 2011;32(22):5134-47. (Year: 2011).*

(Continued)

*Primary Examiner* — Michelle S Horning
(74) *Attorney, Agent, or Firm* — Ice Miller LLP

(57) ABSTRACT

Methods for inducing anti-phosphorylated Tau antibodies without inducing a severe adverse event in humans are described. The methods include administering to the subject an effective amount of liposomes including a toll-like receptor 4 agonist and a Tau phosphopeptide presented on the surface of the liposome.

20 Claims, 4 Drawing Sheets

Specification includes a Sequence Listing.

(52) U.S. Cl.
CPC ............... *A61K 2039/545* (2013.01); *A61K 2039/55516* (2013.01); *A61K 2039/55555* (2013.01); *A61K 2039/55561* (2013.01); *A61K 2039/55572* (2013.01); *A61K 2039/6018* (2013.01); *A61K 2039/627* (2013.01)

(56) References Cited

U.S. PATENT DOCUMENTS

| | | | |
|---|---|---|---|
| 7,741,297 | B2 | 6/2010 | Jiang |
| 8,647,631 | B2 | 2/2014 | Pfeifer |
| 9,687,447 | B2 | 6/2017 | Reis |
| 11,124,552 | B2* | 9/2021 | Ramsburg .......... A61K 38/1709 |
| 2002/0086009 | A1 | 7/2002 | Ishiguro et al. |
| 2003/0232758 | A1* | 12/2003 | St. George-Hyslop ............... A61P 25/00 514/17.7 |
| 2004/0265920 | A1 | 12/2004 | Seubert et al. |
| 2005/0038239 | A1* | 2/2005 | Catchpole ............... A61P 35/00 435/6.16 |
| 2005/0221391 | A1 | 10/2005 | Davies |
| 2005/0261475 | A1 | 11/2005 | Tseng et al. |
| 2006/0073158 | A1 | 4/2006 | Nicolau et al. |
| 2008/0050383 | A1 | 2/2008 | Sigurdsson et al. |
| 2008/0220449 | A1 | 9/2008 | Vasan et al. |
| 2010/0316564 | A1 | 12/2010 | Sigurdsson et al. |
| 2012/0183599 | A1 | 7/2012 | Pfeifer |
| 2016/0347804 | A1 | 12/2016 | Griswold-Prenner |
| 2019/0112362 | A1 | 4/2019 | Adolfsson |
| 2019/0119341 | A1 | 4/2019 | Ramsburg |
| 2020/0339643 | A1 | 10/2020 | Ramsburg et al. |
| 2020/0376078 | A1* | 12/2020 | Ramsburg ............. A61K 9/1271 |
| 2021/0388044 | A1 | 12/2021 | Ramburg et al. |

FOREIGN PATENT DOCUMENTS

| | | | |
|---|---|---|---|
| WO | 1996020218 | A1 | 7/1996 |
| WO | 1997034145 | A1 | 9/1997 |
| WO | 1998022120 | A1 | 5/1998 |
| WO | 2003066649 | A1 | 8/2003 |
| WO | 2005080986 | A1 | 9/2005 |
| WO | 2005081872 | A2 | 9/2005 |
| WO | 2007068105 | A1 | 6/2007 |
| WO | 2007068411 | A2 | 6/2007 |
| WO | 2010106127 | A2 | 9/2010 |
| WO | 2010115843 | A2 | 10/2010 |
| WO | 2010144711 | A2 | 12/2010 |
| WO | 2011013034 | A1 | 2/2011 |
| WO | 2012020124 | A1 | 2/2012 |
| WO | 2012055933 | A1 | 5/2012 |
| WO | 2015197823 | A2 | 12/2015 |
| WO | 2018106781 | A1 | 6/2018 |
| WO | 2019084118 | A2 | 5/2019 |
| WO | 2019094595 | A2 | 5/2019 |

OTHER PUBLICATIONS

Zheng-Fischhoefer et al., "Sequential Phosphorylation of Tau by Glycogen Synthase Kinase-3beta and Protein Kinase A at Thr212 and Ser214 Generates the Alzheimer-Specific Epitope of Antibody AT100 and Requires a Paired-Helical-Filament-Like Conformation," European Journal of Biochemistry, vol. 252, No. 3, pp. 542-552 (1998).

Invitation to Pay Additional Fees dated May 27, 2020 in International Application No. PCT/US2020/017235.

Alving C R, "Antibodies to Liposomes Phospholipids and Phosphate Esters", Chemistry and Physics of Lipids, (1986), vol. 40, No. 2-4, doi:doi:10.1016/0009-3084(86)90075-7, ISSN 0009-3084, pp. 303-314, XP025418929.

Andronesi Ovidiu C et al, "Characterization of Alzheimer's-like paired helical filaments from the core domain of tau protein using solid-state NMR spectroscopy", Journal of the American Chemical Society, (May 2008), vol. 130, No. 18, ISSN 0002-7863, pp. 5922-5928.

Boutajangout Allal et al, "Immunotherapy Targeting Pathological Tau Prevents Cognitive Decline in a New Tangle Mouse Model", Journal of Neuroscience, (Dec. 2010), vol. 30, No. 49, doi:doi:10.1523/JNEUROSCI.4363-10.2010, ISSN 0270-6474, pp. 16559-16566, XP055203597.

Wassef N M et al, "Phosphate-Binding Specificities of Monoclonal Antibodies Against Phosphoinositides in Liposomes", Molecular Immunology, (1984), vol. 21, No. 10, doi:doi:10.1016/0161-5890(84)90140-8, ISSN 0161-5890, pp. 863-868, XP023786303.

Shane Crotty, "Follicular helper CD4 T cells (TFH)", Annu. Rev. Immunol. 2011, 29, 621-663, www.annualreviews.org.

Greenberg et al., "A preparation of Alzheimer paired helical filaments that displays distinct T proteins by polyacrylamide gel electrophoresis", Proc. Natl. Acad. Sci. USA, vol. 87, pp. 5827-5831, Aug. 1990.

Peeraer et al., "Intracerebral injection of preformed synthetic tau fibrils initiates widespread tauopathy and neuronal loss in the brains of tau transgenic mice", Neurobiol. Dis. Jan. 2015, 73, 83-95.

Spensieri et al., "Human circulating influenza-CD4+ICOS1+IL-21+ T cells expand after vaccination, exert helper function, and predict antibody responses", PNAS, vol. 110, No. 35, 14330-14335, Aug. 27, 2013.

Bentebibel et al., "Induction of ICOS+CXCR3+CXCR5+TH cells correlates with antibody responses to influenza vaccination", Sci Transl Med Mar. 13, 2013, 5(176), 19 pages.

Asuni et al., "Immunotherapy Targeting Pathological Tau Conformers in a tangle Mouse Model Reduces Brain Pathology with Associated Functional Improvements," Journal of Neuroscience, vol. 27, No. 34, pp. 9115-9129 (2007).

Bhaskar et al., "Tyrosine Phosphorylation of Tau Accompanies Disease Progression in Transgenic Mouse Models of Tauopathy," Neuropathology and Applied Neurobiology, vol. 36, No. 6, pp. 462-477 (2012).

Boimel et al., "Efficacy and safety of immunization with phosphorylated tau against neurofibrillary tangles in mice," Experimental Neurology, vol. 224, pp. 472-485 (2010).

Clinical Trials, "Safety Study of AADvac1, a Tau Peptide-KLH-Conjugate Active Vaccine to Treat Alzheimer's Disease", https://www.clinicaltrials.gov/ct2/show/record/nct018502387view=record, ClinicalTrials.gov Identifier: NCT01850238, Oct. 2015.

De Titta et al., "Nanoparticle Conjungation of CpG Enhances Adjuvancy from Cellular Immunity and Memory Recall at Low Dose", PNAS, vol. 110, No. 49, pp. 19902-19907 (2013).

Dominguez et al., "Novel Therapeutic Strategies Provide the Real Test for the Amyloid Hypothesis Alzheimer's Disease," Trends in Pharmacological Sciences, vol. 23, No. 7, pp. 324-330 (2002).

Friedhoff et al., "Structure of tau protein and assembly into paired helical filaments", Biochimica et Biophysica Acta, 1502, pp. 122-132, 2000.

Gandhi et al., "A Phosphorylation-Induced Turn Defines the Alzheimer's Disease AT8 Antibody Epitope on the Tau Protein," Angew Chem Int Ed Engl, vol. 54, No. 23, pp. 6819-6823 (2015).

Hanger et al., "Tau phosphorylation: the therapeutic challenge for neurodegenerative disease" Trends in Molecular Medicine, vol. 15, No. 3, pp. 112-119 (2009).

Hickman et al., "Sequence-independent Conftrol of Peptide Conformation in Liposomal Vaccines for Targeting Protein Misfolding Diseases," The Journal of Biological Chemistry, vol. 286, No. 16, pp. 13966-13976 (2011).

Hills et al., "A Rapid-Response Humoral Vaccine Platform Exploiting pre-Existing Non-Cognate Populations of Anti-Vaccine or Anti-Viral CD4+ T Helper Cells to confirm B Cell Activation," PLoS One, 20 pages, Nov. 18, 2016.

Hirata-Fukae et al., "Levels of Soluble and Insoluble Tau Reflect Overall Status of Tau Phosphorylation in Vivo," Neuroscience Letters, vol. 450, No. 1, pp. 51-55 (2009).

Hoffman et al., "Unique Alzheimer's Disease Paired Helical Filament Specific Epitopes Involve Double Phosphorylation at Specific Sites," Biochemistry, vol. 36, No. 26, pp. 8114-8124 (1997).

(56) References Cited

OTHER PUBLICATIONS

Jicha et al., "Camp-Dependent Protein Kinase Phosphorylations on Tau in Alzheimer's Disease," Journal of Neuroscience, vol. 19, No. 17, pp. 7486 (1999).
Kontsekova et al., "Identification of structural determinants on tau protein essential for its pathological function: novel therapeutic target for tau immunotherapy in Alzheimer's Disease," Alzheimer's research & therapy, vol. 6, No. 45, pp. 1-16 (2014).
Lee et al., "Phosphorylation of Tau by Fyn: Implications for Alzheimer's Disease," Journal of Neuroscience, Mar. 3, 2004, vol. 24, No. 9, pp. 2304-2312.
Lewis et al., "Neurofibrillary Tangles, Amyotrophy and Progressive Motor Disturbance in Mice Expressing Mutant (P301L) Tau Protein," Nature America, Inc., vol. 25, pp. 402-405 (2000).
Lichtenberg-Kraag et al., "Phosphorylation-Dependent Epitopes of Neurofilament Antibodies on Tau Protein and Relationship with Alzheimer Tau," PNAS, vol. 89, No. 12, pp. 5384-5388 (1992).
Masliah et al., "Effects of a-Synuclein Immunization in a Mouse Model of Parkinson's Disease," Neuron, vol. 46, pp. 857-868 (2005).
Maiyas et al., "Liposomes containing monophosphoryl lipid A: A Potent adjuvant system for inducing antibodies to heroin hapten analogs", Vaccine, vol. 21, pp. 2804-2810 (2013).
Muhs et al., "Liposomal Vaccines with Conformation-Specific Amyloid Peptide Antigens Define Immune Response and Efficacy in APP Transgenic Mice," PNAS, vol. 104, No. 23, pp. 9810-9815 (2007).
Muyllaert et al., "Glycogen Synthase Kinase-3p, or a Link Between Amyloid and Tau Pathology?" Genes, Brain and Behavior, vol. 7, Suppl. 1, pp. 57-66 (2008).
Muyllaert et al., "Transgenic Mouse Models for Alzheimer's Disease: the Role of GSK-3p in Combined Amyloid and Tau-Pathology," Rev Neurol (Paris), vol. 162, No. 10, pp. 903-907 (2006).
Nakamura et al., "Cisphosphorylated tau as the earliest detectable pathogenic conformation in Alzheimer disease, offering novel diagnostic and therapeutic strategies," Prion, vol. 7, No. 2, pp. 117-120 (2013).
Neeland et al., "Incorporation of CpG into a Liposomal Vaccine Formulation Increases the Maturation of Antigen-Loaded dendritic Cells and Monocytes to Improve Local and Systemic Immunity", Journal of Immunology, vol. 192, pp. 3666-3675 (2014).
Nicolau et al., "A Liposome-Based Therapeutic Vaccine Against (3-Amyloid Plaques on the Pancreas of Transgenic Mice," PNAS, vol. 99, No. 4, pp. 2332-2337 (2012).
Nicoll et al., "Neuropathology of Human Alzheimer Disease After Immunization with Amyloid-p Peptide: A Case Report," Nature Medicine, vol. 9, No. 4, pp. 448-452 (2003).
Novak et al., "Characterisation of the Antibody Response to Aadvac1: The First-in-Kind Active Vaccine Against Neurofibrillary Tau Pathology", Alzeheimer's & Dementia: The Journal of The Alzheimer's Association, vol. 12, No. 7, pp. P351 (2016).
Novak et al., "Safety and immunogenicity of the tau vaccine AADvac1 in patients with Alzheimer's disease: randomised, double-blind, placebo-controlled, phase 1 trail," Lancet Neurol, vol. 16, pp. 123-134 (2017).
Oddo et al., "A-beta Immunotherapy Leads to Clearance of Early, but Not Late, Hyperphosporylated Tau Aggregates via the Proteasome," Neuron, vol. 43, pp. 321-332 (2004).
Oddo et al., "Reduction of Soluble Abeta and Tau, but Not Soluble Abeta Alone, Ameliorates Cognitive Decline in Transgenic Mice with Plaques and Tangles," Journal of Biological Chemistry, vol. 281, No. 51, pp. 39413-39423 (2006).
Otvos et al., "Monoclonal Antibody PHF4 Recognizes Tau Protein Phosphorylated at Serine Residues 396 and 404," Journal of Neuroscience Research, vol. 39, pp. 669-673 (1994).
Ribe et al., "Accelerated Amyloid Deposition, Neurofibrillary Degeneration and Neuronal Loss in Double Mutant APP/Tau Transgenic Mice," Neurobiology of Disease, vol. 20, pp. 814-822 (2005).
Richter et al., "Doubly Phosphorylated Peptide Vaccines to Protect Transgenic P301S Mice against Alzheimer's Disease Like Tau Aggregation", Vaccines, vol. 2, pp. 601-623 (2014).
Ries et al., "Convenient synthesis and application of versatile nucleic acid lipid membrane anchors in the assembly and fusion of liposomes", Organic & Biomolecular Chemistry, vol. 13, pp. 9673-9680 (2015).
Roberson et al., "Reducing Endogenous Tau Ameliorates Amyloid (3-Induced Deficits in an Alzheimer's Disease Mouse Model," Science, vol. 316, pp. 750-754 (2007).
Roder et al., "Phosphorylation-Dependent Monoclonal Tau Antibodies Do Not Reliably Report Phosphorylation by Extracellular Signal-Regulated Kinase 2 at Specific Sites," Journal of Biological Chemistry, vol. 272, No. 7, pp. 4509-4515 (1997).
Roman et al., "Therapeutic Vaccination Using Cationic Liposome-Adjuvanted HIV Type 1 Peptides Representing HLA-Supertype-Restricted Subdominant T Cell Epitopes: Safety, Immunogenicity, and Feasibility in Guinea-Bissau," AIDS Research and Human Retroviruses, vol. 29, No. 11, pp. 1504-1512 (2013).
Rosenmann et al., "Tauopathy-Like Abnormalities and Neurologic Deficits in Mice Immunized with Neuronal Tau Protein," Arch Neurol, vol. 63, pp. 1459-1467 (2006).
Rueda et al., "Effect of TLR ligands co-encapsulated with multiepitopic antigen in nanoliposomes tartgeted to human DCs via Fc receptor for cancer vaccines," Immunobiology, vol. 222, pp. 989-997 (2017).
Sela et al., "Therapeutic Vaccines: Realities of Today and Hopes forthe Future," Drug Discovery Today—Reviews, Therapeutic Focus, vol. 7, No. 12, pp. 664-673 (2002).
Singer et al., "Characterization of Phosphorylation Dependent Antibodies to Study the Phosphorylation Dependent Antibodies to Study the Phosphorylation Status of the Tau Protein," International Journal of Peptide Research and Therapeutics (formerly known as Letters in Pepdtide Science), vol. 11, No. 4, pp. 279-289 (2005).
Singer et al., "Immuno-PCR-Based Quantification of Multiple Phosphorylated Tau-Epitopes Linked to Alzheimer's Disease," Analytical and Bioanalytical Chemistry, vol. 395, No. 7, pp. 2263-2267 (2009).
Tabira, "Immunization Therapy for Alzheimer Disease: A Comprehensive Review of Active Immunization Strategies," Tohoku J. Exp. Med., vol. 220, pp. 95-106 (2010).
Terwel et al., "Amyloid Activates GSK-3p to Aggravate Neuronal Tauopathy in Bigenic Mice," The American Journal of Pathology, vol. 172, No. 3, pp. 786-798 (2008).
Theunis et al., "Efficacy and Safety of a Liposome-Based vaccine against Protein Tau, Assessed in Tau. P301 L Mice That Model Tauopathy," PLoS One, vol. 8, Issue 8, pp. e72301, 13 pages (2013).
Theunis et al., "Novel Phospho-Tau monoclonal Antibody Generated Using a Liposomal Vaccine, with Enhanced Recognition of Conformational Tauopathy Epitope", Journal of Alzheimer's Disease, vol. 56, No. 2, pp. 585-599 (2017).
Torreilles et al., "Binding Specificity of Monoclonal Antibody AD2: Influence of the Phosphorylation State of Tau," Molecular Brain Research, vol. 78, pp. 181-185 (2001).
VanHelmont et al., "Serine-409 Phosphorylation and Oxidative Damage Define Aggregation of Human Protein Tau in Yeast," Fems Yeast Research, vol. 10, No. 8, pp. 992-1005 (2010).
Zemlan et al., "Monoclonal Antibody PHF-9 Recognizes Phosphorylated Serine 404 of Tau Protein and Labels Paired Helical Filaments," Journal of Neuroscience Research, vol. 46, No. 1, pp. 90-97 (1996).
Dubois, Bruno, et al., "Preclinical Alzheimer's disease: Definition, natural history, and diagnostic criteria", Alzheimers Dement. 12(3), 292-323, 2016.
Novak, Petr, et al., "Fundamant: an interventional 72-week phase 1 follow-up study of AADvad1, an active immunotherapy against tau protein pthology in Alzheimer's disease", Alzheimer's Research & Therapy, 10:108, 2018.
Novak, Petr, et al., "Ten Years of Tau-Targeted Immunotherapy: The Path Walked and the Roads Ahead", Front. Neurosci., 12, 798, 2018.
Orgogozo, M.D., J.M., et al., "Subacute meningoencephalitis in a subset of patients with AD after AB42 immunization", Neurology 61, 46-54, 2003.

(56) References Cited

OTHER PUBLICATIONS

Rosenmann, Hanna, "Immunotherapy for Targeting Tau Pathology in Alzheimer's Disease and Tauopathier", Current Alzheimer Research, 10, 217-228, 2013.

Sigurdsson, Einar M., "Tau Immunotherapy", Neurodegener Dis., 16(0), 34-38, 2016.

Dubois, Bruno, et al., "Advancing research diagnostic criteria for Alzheimer's disease: the IWG-2 criteria", Lancet Neurol, 13, 614-629, 2014.

Jack, Jr., Clifford R., et al., "NIA-AA Research Framework: Toward a biological definition of Alzheimer's disease", Alzheimer's & Dementia, 14, 535-562, 2018.

Davtyan, Hayk, et al., "MultiTEP platform-based AD epitope vaccine activates broad repertoire of T helper cells in non-human primates", Alzheimers Dement. 10;3, 271-283, 2014.

\* cited by examiner

METHOD OF SAFE ADMINISTRATION OF PHOSPHORYLATED TAU PEPTIDE VACCINE

REFERENCE TO SEQUENCE LISTING SUBMITTED ELECTRONICALLY

This application contains a sequence listing, which is submitted electronically via EFS-Web as an ASCII formatted sequence listing with a file name "065794_5US2", creation date of Oct. 26, 2022, and having a size of 22.3 KB. The sequence listing submitted via EFS-Web is part of the specification and is herein incorporated by reference in its entirety.

FIELD OF THE INVENTION

The present invention is in the field of medicine. The invention in particular relates to liposomes of phosphorylated Tau (pTau) peptides and the use thereof for preventing or treating Tauopathy, such as Alzheimer's disease.

BACKGROUND

Alzheimer's disease (AD) is a progressive debilitating neurodegenerative disease that affects an estimated 44 million people worldwide (Alzheimers.net). AD therapies that are currently commercialized aim to act on the clinical symptoms, but do not target the pathogenic processes that underlie the disease (disease-modifying effect). Unfortunately, the current therapies are only minimally efficacious, and there is therefore an urgent need to develop and test additional preventive and therapeutic measures.

The hallmark pathologies for Alzheimer's disease are an accumulation of extracellular plaques comprising notably aggregated amyloid beta protein and intracellular "tangles" or aggregations of hyperphosphorylated Tau protein. The molecular events that lead to accumulation of these proteins are poorly characterized. For amyloid, it is hypothesized that aberrant cleavage of the amyloid precursor protein leads to an accumulation of the aggregation-prone fragment comprising amino acids 1-42. For Tau, it is hypothesized that dysregulation of either kinases, phosphatases, or both, leads to aberrant phosphorylation of Tau. Once Tau becomes hyperphosphorylated it loses the ability to effectively bind and stabilize microtubules, and instead accumulates in the cytoplasm of the affected neuron. The unbound and hyperphosphorylated Tau appears to form first oligomers and then higher order aggregates, the presence of which presumably negatively affects the function of the neuron in which they form, perhaps via interruption of normal axonal transport.

In developed nations, individuals diagnosed with Alzheimer's disease or other dementing Tauopathies are commonly treated with cholinesterase inhibitors (e.g. Aricept®) or memantine (e.g. Namenda™). These drugs, although reasonably well tolerated, have very modest efficacy. For example, Aricept® delays the worsening of symptoms for 6-12 months in approximately 50% of the treated individuals. The remainder of treatment is non-pharmacologic, and focuses on making patients more capable of managing day to day tasks as their cognitive ability declines.

Immunotherapies are currently under development for the prevention and treatment of AD. Active immunization with an antigen related to AD can potentially stimulate a response of both antibody-based and cellular immunity against AD. However, evaluation of the first widely tested human anti-amyloid beta vaccine was stopped in 2002. Meningoencephalitis, a type of central nervous system inflammation that can be fatal, was observed in clinical studies in AD patients of the active immunotherapeutic agent AN-1792 that targeted Aβ (Orgogozo et al., 2003). The encephalitic reactions, which occurred in 6% of patients exposed to the AN-1792, are thought to have been induced by unwanted Aβ-specific T-cell activation.

To date few studies have been conducted with agents specifically targeting Tau pathology. Tau immunotherapies are now moving into clinical trials but the field is still in its infancy and mechanistic understanding of the efficacy and safety of the various approaches is not well established (Sigurdsson, Neurodegener Dis. 2016; 16(0): 34-38). Encephalitis, inflammation of the brain, has also been reported in mice immunized against full-length Tau protein. However, no adverse effects were reported from animals immunized with a single injection of phosphorylated-Tau peptide under a CNS proinflammatory milieu (Rosenmann H., 2013. Curr. Alzheimer Res. 10, 217-228).

The long-term safety profile of a non-phosphorylated Tau peptide vaccine (AADvac1) in human patients with mild to moderate Alzheimer's disease has been recently published (Novak et al., Alzheimer's Research & Therapy (2018) 10:108). The vaccine contains a synthetic peptide derived from amino acids 294 to 305 of the Tau sequence coupled to keyhole limpet hemocyanin (KLH) through an N-terminal cysteine. It was administered in doses of 40 μg of the peptide of SEQ ID NO: 45 (CKDNIKHVPGGGS) coupled to KLH, with aluminium hydroxide adjuvant (containing 0.5 mg $Al^{3+}$) in a phosphate buffer volume of 0.3 ml. The observed adverse events (AEs) from the 26 patients enrolled in the study and linked to AADvac1 treatment in the phase 1 study (FUNDAMANT study) were injection site reactions (erythema, swelling, warmth, pruritus, pain, nodule). One or more of these AEs were observed in 50% of patients on AADvac1 treatment. Injection site reactions were reversible and predominantly mild in presentation. Six severe adverse events (SAEs) were observed (abdominal strangulated hernia, dehydration, acute psychosis, behavioral and psychiatric symptoms of dementia, second-degree atrioventricular block, and sinus bradycardia). None of the SAEs were judged by the investigators to be related to AADvac1 treatment. No allergic or anaphylactic reactions were observed. No safety signals emerged in laboratory assessment (coagulation, blood biochemistry, hematology, and urinalysis), vital sign assessment, or neurological and physical examination. No safety signals were detected by MM assessment. No oedematous changes occurred. No meningeal changes and no meningoencephalitis were observed. New micro-hemorrhages were observed in one ApoE4 homozygote, and superficial hemosiderin was detected in one ApoE4 heterozygote, both events were clinically silent. This was considered to be consistent with the background incidence of such lesions in the AD patient population.

However, the safety profile of phosphorylated Tau peptide vaccine in human patients has not been reported. There is a need for a safe and effective treatment for neuronal degenerative disease, such as Alzheimer's disease.

SUMMARY OF THE INVENTION

The invention is based on findings from clinical studies of a liposomal vaccine comprising a phosphorylated Tau peptide presented on the surface of the liposome. The vaccine appeared well-tolerated in humans. It was shown that at a dose much higher than that used in the Tau conjugate vaccine AADvac1 trial, the pTau peptide liposomal vaccine induced anti-phosphorylated Tau antibodies in the human subjects without inducing a severe adverse event.

Accordingly, in one general aspect, the invention provides a method of inducing anti-phosphorylated Tau antibodies without inducing a severe adverse event, such as encephalitis, in a human subject in need thereof, comprising administering to the subject an effective amount of liposomes comprising a toll-like receptor 4 agonist and a Tau phosphopeptide comprising an amino acid sequence selected from the group consisting of SEQ ID NO:1 to SEQ ID NO:3 and SEQ ID NO:5 to SEQ ID NO:12, wherein the Tau phosphopeptide is administered at an amount of about 25 nmoles to about 750 nmoles per dose, such as about 29.7 nmoles to about 742.5 nmoles per dose, preferably about 90 nmoles to about 715 nmoles, such as about 89.1 nmoles to about 712.8 nmoles per dose, or about 90 nmoles to about 535 nmoles per dose, such as about 89.1 nmoles to about 534.6 nmoles per dose, or about 90 nmoles to about 275 nmoles per dose, such as about 89.1 nmoles to about 267.3 nmoles per dose, and wherein the Tau phosphopeptide is presented on the surface of the liposome. In certain embodiments, the Tau phosphopeptide consists of an amino acid sequence selected from the group consisting of SEQ ID NO:27 to SEQ ID NO:29 and SEQ ID NO:31 to SEQ ID NO:38, preferably consists of an amino acid sequence of SEQ ID NO:28. In one embodiment, the effective amount of liposomes comprises a toll-like receptor 4 agonist and a tetrapalmitoylated Tau phosphopeptide consisting of the amino acid sequence of SEQ ID NO: 28, wherein the tetrapalmitoylated Tau phosphopeptide is presented on the surface of the liposome and is administered at an amount of 100 μg to 2500 μg per dose, corresponding to 29.7 nmoles to 742.5 nmoles per dose, preferably 300 μg to 2400 μg per dose, corresponding to 89.1 nmoles to 712.8 nmols per dose, such as 300 μg, 900 μg, 1800 μg or 2400 μg per dose, corresponding to 89.1 nmoles, 267.3 nmoles, 534.6 nmoles or 712.8 nmoles per dose.

In some embodiments, the invention provides a method of inducing anti-phosphorylated Tau antibodies without inducing a severe adverse event, such as encephalitis, in a human subject in need thereof, comprising administering to the subject an effective amount of liposomes comprising a toll-like receptor 4 agonist and a Tau phosphopeptide presented on the surface of the liposome, wherein the Tau phosphopeptide comprises an amino acid sequence selected from the group consisting of SEQ ID NO:1 to SEQ ID NO:3 and SEQ ID NO:5 to SEQ ID NO:12 and the Tau phosphopeptide is administered at an amount of about 25 nmoles to about 750 nmoles per dose, preferably the Tau phosphopeptide is a tetrapalmitoylated Tau phosphopeptide consisting of the amino acid sequence of SEQ ID NO: 28 and is administered at an amount of about 300 μg, about 900 μg, about 1800 μg or about 2400 μg, per dose, or any amount in between.

In certain embodiments, the method of inducing anti-phosphorylated Tau antibodies without inducing a severe adverse event, such as encephalitis, in a human subject in need thereof, comprising administering to the subject an effective amount of liposomes comprising a toll-like receptor 4 agonist and a Tau phosphopeptide presented on the surface of the liposome, wherein the Tau phosphopeptide comprises an amino acid sequence selected from the group consisting of SEQ ID NO:27 to SEQ ID NO:29 and SEQ ID NO:31 to SEQ ID NO:38, and the Tau phosphopeptide is administered at an amount of about 90 nmoles to about 715 nmoles per dose, such as about 29.7 nmoles, about 267.3 nmoles, about 534.6 nmoles, or about 712.8 nmoles per dose, or any amount in between. In one embodiment, the effective amount of liposomes comprises the Tau phosphopeptide at an amount of 265 to 275 nmoles per dose, e.g., 265, 266, 267, 268, 269, 270, 271, 272, 273, 274 or 275 nmoles per dose, or any value in between, such as about 267.3 nmoles per dose. In another embodiment, the effective amount of liposomes comprises the Tau phosphopeptide at an amount of 530 to 540 nmoles per dose, such as 530, 531, 532, 533, 534, 535, 536, 537, 538, 539 or 540 nmoles per dose, or any value in between, such as 534.6 nmoles per dose. In another embodiment, the effective amount of liposomes comprises the Tau phosphopeptide at an amount of 710 to 720 nmoles per dose, such as 710, 711, 712, 713, 714, 715, 716, 717, 718, 719 or 720 nmoles per dose, or any value in between, such as 712.8 nmoles per dose.

In certain embodiments, the liposomes are administered subcutaneously.

In certain embodiments, the liposomes are administered intramuscularly.

In certain embodiments, the method further comprises administering to the subject a second dose of the effective amount of liposomes 1 to 24 weeks after the initial administration.

In certain embodiments, the liposome further comprises at least one of a helper T-cell epitope and a lipidated CpG oligonucleotide. In certain embodiments, the lipidated CpG oligonucleotide has a nucleotide sequence selected from the group consisting of SEQ ID NO:18 to SEQ ID NO:22, preferably has a nucleotide sequence of SEQ ID NO:18, wherein the CpG oligonucleotide has one or more phosphorothioate internucleotide linkages, and the CpG oligonucleotide is covalently linked to at least one lipophilic group via a linker, preferably via a PEG linker.

In certain embodiments, the liposome further comprises one or more lipids selected from the group consisting of 1,2-dimyristoyl-sn-glycero-3-phosphocholine (DMPC), 1,2-dimyristoyl-sn-glycero-3-phosphoryl-3'-rac-glycerol (DMPG), and cholesterol.

In certain embodiments, the helper T-cell epitope comprises at least one amino acid sequence selected from the group consisting of SEQ ID NO:23 to SEQ ID NO:26, preferably comprises the amino acid sequences of SEQ ID NO:23 to 25.

In certain embodiments, the toll-like receptor 4 agonist is monophosphoryl lipid A (MPLA).

In certain embodiments, the effective amount of liposomes comprises the toll-like receptor 4 agonist at an amount of 30 μg to 900 μg, preferably 100 μg to 585 μg, per dose. In certain embodiments, the effective amount of liposomes comprises the toll-like receptor agonist monophosphoryl hexa-acyl Lipid A, 3-deacyl at an amount of 30 μg to 900 μg, preferably 100 μg to 585 μg, per dose.

In certain embodiments, the effective amount of liposomes comprises the helper T-cell epitope at an amount of 25 μg to 625 μg, preferably 75 μg to 450 μg, per dose. In certain embodiments, the effective amount of liposomes comprises a T50 helper T-cell epitope consisting of the amino acid sequence of SEQ ID NO: 13 at an amount of 25 μg to 625 μg, preferably 75 μg to 450 μg, per dose.

In certain embodiments, the effective amount of liposomes comprises the helper T-cell epitope at an amount of about 2 nmoles to about 110 nmoles per dose, such as about 4.02 nmoles to about 100.44 nmoles per dose, or about 4 nmoles to about 75 nmoles per dose, such as about 4.02 nmoles to about 72.32 nmoles per dose, or about 10 nmoles to about 105 nmoles per dose, such as about 12.06 nmoles to about 100.44 nmoles per dose, or about 70 to about 105 nmoles per dose, such as about 72.32 nmoles to about 100.44 nmoles per dose. In certain embodiments, the effective amount of liposomes comprises a T50 helper T-cell epitope consisting of the amino acid sequence of SEQ ID NO: 13 at an amount of about 3 nmoles to about 105 nmoles per dose, preferably about 10 nmoles to about 105 nmoles per dose, such as about 12.06 nmoles to about 100.44 nmoles per dose. In one embodiment, the effective amount of liposomes comprises the helper T-cell epitope at an amount of 2 to 5 nmoles per dose, e.g., 2, 3, 4 or 5 nmoles per dose or any value in between, such as about 3.82, 3.92, 4.02 or 4.12 nmoles per dose. In another embodiment, the effective amount of liposomes comprises the helper T-cell epitope at an amount of 10 to 15 nmoles per dose, such as 10, 11, 12, 13, 14 or 15 nmoles per dose, or any value in between, such as 11.86, 11.96, 12.06, 12.16 nmoles per dose. In another embodiment, the effective amount of liposomes comprises the helper T-cell epitope at an amount of 70 to 75 nmoles per dose, such as 70, 71, 72, 73, 74 or 75 nmoles per dose, or any value in between, such as 72.02, 72.12, 72.22, 72.32, 72.42. In yet another embodiment, the effective amount of liposomes comprises the helper T-cell epitope at an amount of 98 to 103 nmoles per dose, such as 98, 99, 100, 101, 102 or 103 nmoles per dose, or any value in between, such as 100.24, 100.34, 100.44, 100.54 or 100.64 nmoles per dose.

In certain embodiments, the effective amount of liposomes comprises the lipidated CpG oligonucleotide at an amount of 50 µg to 1250 µg, preferably 150 µg to 800 µg, per dose. In certain embodiments, the effective amount of liposomes comprises a CpG oligonucleotide consisting of the nucleotide sequence of SEQ ID NO:18 at an amount of 50 µg to 1250 µg, preferably 150 µg to 800 µg, per dose.

In certain embodiments, the liposome comprises:
(1) the Tau phosphopeptide having the amino acid sequence of SEQ ID NO:28;
(2) the toll-like receptor 4 agonist comprising monophosphoryl hexa-acyl Lipid A, 3-deacyl;
(3) the helper T-cell epitope comprising the amino acid sequence of SEQ ID NO: 39;
(4) the lipidated CpG oligonucleotide comprising the nucleotide sequence of SEQ ID NO:18; and
(5) at least one lipid selected from the group consisting of 1,2-dimyristoyl-sn-glycero-3-phosphocholine (DMPC), 1,2-dimyristoyl-sn-glycero-3-phosphoryl-3'-rac-glycerol (DMPG), and cholesterol.

In certain embodiments, the subject is in need of a treatment of Alzheimer's Disease, such as early Alzheimer's Disease, mild cognitive impairment (MCI) due to Alzheimer's Disease, mild Alzheimer's Disease, or mild to moderate Alzheimer's Disease. In other embodiments, the subject is amyloid positive in the brain but does not yet show significant cognitive impairment.

The invention also relates to a vaccine combination for use in inducing anti-phosphorylated Tau antibodies without inducing a severe adverse event, such as encephalitis, in a human subject in need thereof, wherein the vaccine combination comprises a primer vaccine and a booster vaccine according to embodiments of the invention. The invention also provides the use of a vaccine combination in the manufacture of a medicament for inducing anti-phosphorylated Tau antibodies without inducing a severe adverse event, such as encephalitis, in a human subject in need thereof, wherein the vaccine combination comprises a primer vaccine and a booster vaccine according to embodiments of the invention. All aspects and embodiments of the invention as described herein with respect to methods of inducing anti-phosphorylated Tau antibodies without inducing a severe adverse event, such as encephalitis, in a human subject can be applied to the vaccine combinations for use and/or uses of the vaccine combination in the manufacture of a medicament for inducing anti-phosphorylated Tau antibodies without inducing a severe adverse event, such as encephalitis, in a human subject in need thereof.

Further aspects, features and advantages of the present invention will be better appreciated upon a reading of the following detailed description of the invention and claims.

BRIEF DESCRIPTION OF THE FIGURES

The foregoing summary, as well as the following detailed description of preferred embodiments of the present application, will be better understood when read in conjunction with the appended drawings. It should be understood, however, that the application is not limited to the precise embodiments shown in the drawings.

DETAILED DESCRIPTION OF THE INVENTION

Figure 1:
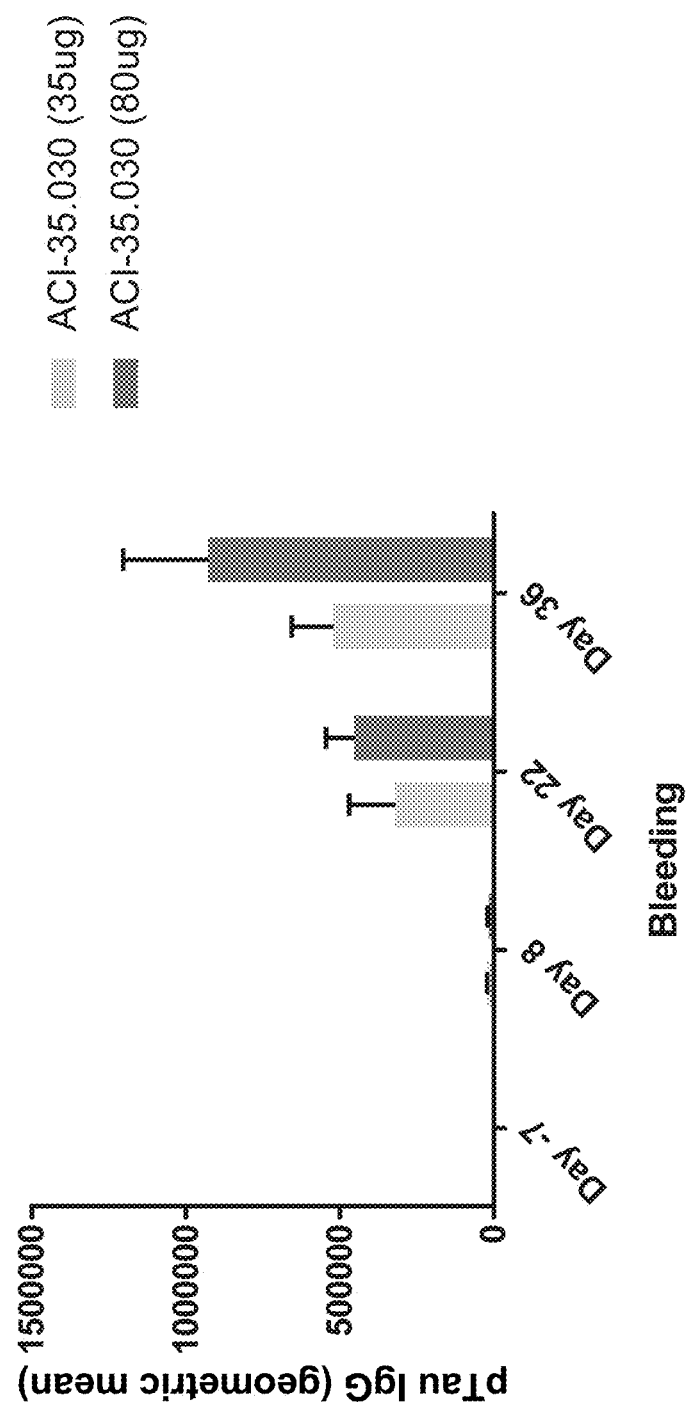
FIG. 1 shows pTau IgG titers following three intramuscular administrations once every two weeks of 35 and 80 µg/dose of ACI-35.030 to female C57BL/6 mice; geometric mean +95% CI per group of 10 mice is represented.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The invention provides a method of inducing anti-phosphorylated Tau antibodies without inducing a severe adverse event, such as encephalitis, in a human subject in need thereof. In particular embodiments, the method comprises administering to the subject an effective amount of liposomes comprising a Tau phosphopeptide presented on the surface of the liposome and a toll-like receptor 4 agonist.

As used herein, the term "anti-phosphorylated Tau antibody" refers to an antibody that binds to Tau that has been phosphorylated on an amino acid residue at one or more locations of the amino acid sequence of Tau. The phosphorylated amino acid residues can be, e.g., serine (Ser), threonine (Thr) or tyrosine (Tyr). The site on phosphorylated Tau to which the anti-phosphorylated Tau antibody binds is preferably a site that is specifically phosphorylated in neurodegenerative diseases such as Alzheimer's Disease. Examples of sites of phosphorylated Tau to which the anti-phosphorylated Tau antibody binds include, for example, Tyr18, Ser199, Ser202, Thr205, Thr212, Ser214, Ser396, Ser404, Ser409, Ser422, Thr427. As used throughout the present application, the amino acid positions are given in reference to the sequence of human microtubule-associated protein tau isoform 2 having the amino acid sequence represented in GenBank Accession No. NP_005901.2.

The ability to induce anti-phosphorylated Tau antibodies upon administration can be determined by testing a biological sample (e.g., blood, plasma, serum, PBMCs, urine, saliva, feces, CSF or lymph fluid) from the subject for the presence of antibodies, e.g. IgG or IgM antibodies, directed to the immunogenic Tau peptide(s) administered in the pharmaceutical composition (see for example Harlow, 1989, Antibodies, Cold Spring Harbor Press). For example, titers of antibodies produced in response to administration of a composition providing an immunogen can be measured by enzyme-linked immunosorbent assay (ELISA), other ELISA-based assays (e.g., MSD-Meso Scale Discovery), dot blots, SDS-PAGE gels, ELISPOT or Antibody-Dependent Cellular Phagocytosis (ADCP) Assay.

As used herein, the term "adverse event" (AE) refers to any untoward medical occurrence in a patient administered a pharmaceutical product and which does not necessarily have a causal relationship with the treatment. According to embodiments of the invention, AEs are rated on a 3-point scale of increasing severity using the following definitions: mild (grade 1), referring to an AE that is easily tolerated by the subject, which causes minimal discomfort and does not interfere with everyday activities; moderate (grade 2), referring to an AE that is sufficiently discomforting to interfere with normal everyday activities and intervention may be needed; severe (grade 3), referring to an AE that prevents normal everyday activities, and treatment or other intervention is usually needed. A severe AE (SAE) can be any AE occurring at any dose that results in any of the following outcomes: death, where death is an outcome, not an event; life-threatening, referring to an event in which the patient is at risk of death at the time of the event; it does not refer to an event which could hypothetically have caused death had it been more severe; in patient hospitalization, i.e., an unplanned, overnight hospitalization, or prolongation of an existing hospitalization; persistent or significant incapacity or substantial disruption of the ability to conduct normal life functions; congenital anomaly/birth defect; important medical event (as deemed by the investigator) that may jeopardize the patients or may require medical or surgical intervention to prevent one of the other outcomes listed above (e.g. intensive treatment in an emergency room or at home for allergic bronchospasm or blood dyscrasias or convulsions that do not result in hospitalization). Hospitalization is official admission to a hospital. Hospitalization or prolongation of a hospitalization constitutes criteria for an AE to be serious; however, it is not in itself considered an SAE. In the absence of an AE, hospitalization or prolongation of hospitalization should not be reported as a SAE by the participating investigator. This can be the case, in the following situations: the hospitalization or prolongation of hospitalization is needed for a procedure required by the protocol; or the hospitalization or prolongation of hospitalization is a part of a routine procedure followed by the center (e.g. stent removal after surgery). This should be recorded in the study file. Hospitalization for elective treatment of a pre-existing condition that did not worsen during the study is not considered an AE.

Complications that occur during hospitalization are AEs. If a complication prolongs hospitalization, or meets any of the other SAE criteria, then the event is an SAE.

As used herein, the term "encephalitis" refers to an inflammation of the brain which can result from infectious and non-infectious causes. As used herein, the term "meningoencephalitis" refers to a condition characterized by infection or inflammation of the brain meninges and of the brain. The diagnosis of encephalitis or meningoencephalitis can be determined by techniques known to those skilled in the art in view of the present disclosure, for example, by clinical, neurological and psychiatric examinations, biological sampling including blood and CSF samplings, MRI scanning and electroencephalography (EEG).

As used herein, the term "liposome" refers generally to a lipid vesicle that is made of materials having high lipid content, e.g., phospholipids, cholesterol. The lipids of these vesicles are generally organized in the form of lipid bilayers. The lipid bilayers generally encapsulate a volume which is either interspersed between multiple onion-like shells of lipid bilayers, forming multilamellar lipid vesicles (MLVs) or contained within an amorphous central cavity. Lipid vesicles having an amorphous central cavity are unilamellar lipid vesicles, i.e., those with a single peripheral bilayer surrounding the cavity. Large unilamellar vesicles (LUVs) generally have a diameter of 100 nm to few micrometer, such as 100-200 nm or larger, while small unilamellar lipid vesicles (SUV) generally have a diameter of less than 100 nm, such as 20-100 nm, typically 15-30 nm.

As used herein, the term "Tau" or "Tau protein", also known as microtubule-associated protein Tau, MAPT, neurofibrillary tangle protein, paired helical filament-Tau, PHF-Tau, MAPTL, MTBT1, refers to an abundant central and peripheral nervous system protein having multiple isoforms. In the human central nervous system (CNS), six major Tau isoforms ranging in size from 352 to 441 amino acids in length exist due to alternative splicing (Hanger et al., *Trends Mol Med.* 15:112-9, 2009). Examples of Tau include, but are not limited to, Tau isoforms in the CNS, such as the 441-amino acid longest Tau isoform (4R2N), also named microtubule-associated protein tau isoform 2, that has four repeats and two inserts, such as the human Tau isoform 2 having the amino acid sequence represented in GenBank Accession No. NP_005901.2. Other examples of Tau include the 352-amino acid long shortest (fetal) isoform (3R0N), also named microtubule-associated protein tau isoform 4, that has three repeats and no inserts, such as the human Tau isoform 4 having the amino acid sequence represented in GenBank Accession No. NP_058525.1. Examples of Tau also include the "big Tau" isoform expressed in peripheral nerves that contains 300 additional residues (exon 4a). Friedhoff et al., *Biochimica et Biophysica Acta* 1502 (2000) 122-132. Examples of Tau include a human big Tau that is a 758 amino acid-long protein encoded by an mRNA transcript 6762 nucleotides long (NM_016835.4), or isoforms thereof. The amino acid sequence of the exemplified human big Tau is represented in GenBank Accession No. NP 058519.3. As used herein, the term "Tau" includes homologs of Tau from species other than human, such as *Macaca Fascicularis* (cynomolgus monkey), rhesus monkeys or Pan troglodytes (chimpanzee). As used herein, the term "Tau" includes proteins comprising mutations, e.g., point mutations, fragments, insertions, deletions and splice variants of full-length wild type Tau. The term "Tau" also encompasses post-translational modifications of the Tau amino acid sequence. Post-translational modifications include, but are not limited to, phosphorylation.

As used herein, the term "peptide" or "polypeptide" refers to a polymer composed of amino acid residues, related naturally occurring structural variants, and synthetic non-naturally occurring analogs thereof linked via peptide bonds. The term refers to a peptide of any size, structure, or function. Typically, a peptide is at least three amino acids long. A peptide can be naturally occurring, recombinant, or synthetic, or any combination thereof. Synthetic peptides can be synthesized, for example, using an automated polypeptide synthesizer. Examples of Tau peptides include any peptide of Tau protein of about 5 to about 30 amino acids in length, preferably of about 10 to about 25 amino acids in length, more preferably of about 16 to about 21 amino acids in length. In the present disclosure, peptides are listed from N to C terminus using the standard three or one letter amino acid abbreviation, wherein phosphoresidues are indicated with "p". Examples of Tau peptides useful in the invention include, but are not limited to, Tau peptides comprising the amino acid sequence of any of SEQ ID NOs: 1-12, or Tau peptides having an amino acid sequence that is at least 75%, 80%, 85%, 90% or 95% identical to the amino acid sequence of any of SEQ ID NOs: 1-12.

As used herein, the term "phosphopeptide" or "phospho-epitope" refers to a peptide that is phosphorylated at one or more amino acid residues. Examples of Tau phosphopeptides include any Tau peptide comprising one or more phosphorylated amino acid residues.

The Tau peptides of the present invention can be synthesized by solid phase peptide synthesis or by recombinant expression systems. Automatic peptide synthesizers are commercially available from numerous suppliers, such as Applied Biosystems (Foster City, Calif.). Recombinant expression systems can include bacteria, such as *E. coli*, yeast, insect cells, or mammalian cells. Procedures for recombinant expression are described by Sambrook et al., Molecular Cloning: A Laboratory Manual (C.S.H.P. Press, NY 2d ed., 1989).

According to particular embodiments, the liposome comprises one or more Tau peptides. According to particular embodiments, the Tau peptides in the liposome can be the same or different. Any suitable Tau peptide known to those skilled in the art can be used in the invention in view of the present disclosure. According to particular embodiments, one or more of the Tau peptides comprise the amino acid sequence of one of SEQ ID NOs: 1-12. In other embodiments, one or more of the Tau peptides comprise an amino acid sequence that is at least 75%, 80%, 85%, 90% or 95% identical to the amino acid sequence of one of SEQ ID NOs: 1-12, wherein none of the amino acid residues are phosphorylated, or one or more amino acid residues are phosphorylated.

According to particular embodiments, one or more of the Tau peptides are Tau phosphopeptides. According to particular embodiments, the one or more Tau phosphopeptides comprise the amino acid sequence of one of SEQ ID NOs: 1-3 or 5-12, or an amino acid sequence that is at least 75%, 80%, 85%, 90% or 95% identical to the amino acid sequence of one of SEQ ID NOs: 1-3 or 5-12, wherein one or more of the indicated amino acid residues are phosphorylated. Preferably, the Tau phosphopeptide comprises the amino acid sequence of one of SEQ ID Nos: 1-3. The Tau peptide can have the C-terminus amidated.

According to embodiments of the application, a Tau peptide is presented on the surface of the liposome. A Tau peptide, preferably a Tau phosphopeptide, can be presented on the surface of the liposome using methods known in the art in view of the present disclosure. See, for example, the relevant disclosure in U.S. Pat. Nos. 8,647,631 and 9,687,447, and International Patent Application No. PCT/US18/57286, the content of which is incorporated herein by reference. According to particular embodiments, the one or more Tau peptides, including phosphopeptides, further comprise one or more modifications, such as palmitoylation or dodecyl modification to allow the Tau peptides to be presented on the surface of the liposome. Additional amino acid residues, such as Lys, Cys, or sometimes Ser or Thr, can be added to the Tau peptide to facilitate the modification. It was reported that the position of lipid anchors induces different conformations of the peptide sequence (Hickman et al., J. Biol. Chem. vol. 286, NO. 16, pp. 13966-13976, Apr. 22, 2011). While not wishing to be bound by theory, it is believed that adding hydrophobic moieties at both termini may increase the pathological beta-sheet conformation of the Tau peptide. Thus, the one or more Tau peptides further comprise hydrophobic moieties at both termini. The modified Tau peptide can have the C-terminus amidated. Preferably, a Tau peptide presented on the surface of the liposome consists of the amino acid sequence of one of SEQ ID NO:27 to SEQ ID NO:38.

Examples of tau liposomes useful for the present invention include, but are not limited, tau liposomes described in U.S. Pat. Nos. 8,647,631 and 9,687,447, and International Patent Application No. PCT/US18/57286, the disclose of each is herein incorporated by reference in its entirety.

As used herein, the term "effective amount" refers to an amount of an active ingredient or component that elicits the desired biological or medicinal response in a subject. Selection of a particular effective dose can be determined (e.g., via clinical trials) by those skilled in the art based upon the consideration of several factors, including the disease to be treated or prevented, the symptoms involved, the patient's body mass, the patient's immune status and other factors known by the skilled artisan. The precise dose to be employed in the formulation will also depend on the mode of administration, route of administration, target site, physiological state of the patient, other medications administered and the severity of disease, and should be decided according to the judgment of the practitioner and each patient's circumstances. For example, the effective amount of tau phosphopeptide also depends on whether adjuvant is also administered, with higher dosages being required in the absence of adjuvant. Effective doses can be extrapolated from dose-response curves derived from in vitro or animal model test systems.

According to embodiments of the application, an effective amount of liposomes comprises an amount of Tau phosphopeptide that is sufficient to increase a level of anti-phosphorylated Tau antibodies, without inducing a severe adverse event, such as encephalitis. In particular embodiments, an effective amount of liposomes comprises a Tau phosphopeptide at an amount of about 25 nmoles to about 750 nmoles per dose, such as about 29.7 nmoles to about 742.5 nmoles per dose, preferably about 90 nmoles to about 715 nmoles per dose, such as about 89.1 nmoles to about 712.8 nmoles per dose, or about 90 nmoles to about 535 nmoles per dose, such as about 89.1 nmoles to about 534.6 nmoles per dose, or about 90 nmoles to about 275 nmoles per dose, such as about 89.1 nmoles to about 267.3 nmoles per dose. The amount of Tau phosphopeptide administered can also be expressed by weight. For example, 29.7 nmoles per dose corresponds to 100 µg per dose of a tetrapalmitoylated Tau phosphopeptide consisting of the amino acid sequence of SEQ ID NO: 28, 742.5 nmoles per dose corresponds to 2500 µg per dose of a tetrapalmitoylated Tau phosphopeptide consisting of the amino acid sequence of SEQ ID NO: 28, 89.1 nmoles per dose corresponds to 300 µg per dose of a tetrapalmitoylated Tau phosphopeptide consisting of the amino acid sequence of SEQ ID NO: 28, 712.8 nmoles per dose corresponds to 2400 µg per dose of a tetrapalmitoylated Tau phosphopeptide consisting of the amino acid sequence of SEQ ID NO: 28, and 534.6 nmoles per dose corresponds to 1800 µg per dose of a tetrapalmitoylated Tau phosphopeptide consisting of the amino acid sequence of SEQ ID NO: 28. The tetrapalmitoylated Tau phosphopeptide has four lipidic chains that allow the presentation of the Tau phosphopeptide on the surface of the liposomes. The doses of 300, 900, 1800 µg of tetrapalmitoylated Tau phosphopeptide consisting of the amino acid sequence of SEQ ID NO: 28 correspond to 169, 508, 1016 µg, respectively of the corresponding "naked" peptide without any of the lipidic chains.

According to embodiments of the application, an effective amount of liposomes comprises a Tau phosphopeptide at an amount of about 25 nmoles to about 750 nmoles per dose, such as about 25 nmoles, about 30 nmoles, about 35 nmoles, about 40 nmoles, about 45 nmoles, about 50 nmoles, about 55 nmoles, about 60 nmoles, about 65 nmoles, about 70 nmoles, about 75 nmoles, about 80 nmoles, about 85 nmoles, about 90 nmoles, about 95 nmoles, about 100 nmoles, about 125 nmoles, about 150 nmoles, about 175 nmoles, about 200 nmoles, about 225 nmoles, about 250 nmoles, about 275 nmoles, about 300 nmoles, about 325 nmoles, about 350 nmoles, about 375 nmoles, about 400 nmoles, about 425 nmoles, about 450 nmoles, about 475 nmoles, about 500 nmoles, about 525 nmoles, about 550 nmoles, about 575 nmoles, about 600 nmoles, about 625 nmoles, about 650 nmoles, about 675 nmoles, about 700 nmoles, about 725 nmoles, about 750 nmoles per dose of a Tau phosphopeptide comprising the amino acid sequence of one of SEQ ID NOs: 1-3 or 5-12. Preferably, the Tau phosphopeptide consists of the amino acid sequence of one of SEQ ID NO:27 to SEQ ID NO:38. More preferably, the Tau phosphopeptide consists of the amino acid sequence of SEQ ID NO:28.

According to embodiments of the application, an effective amount of liposomes comprises a tetrapalmitoylated Tau phosphopeptide at an amount of 100 µg to 2500 µg, 300 µg to 2400 µg, 300 µg to 1800 µg, or 300 µg to 900 µg per dose, such as 100 µg, 150 µg, 200 µg, 250 µg, 300 µg, 400 µg, 500 µg, 600 µg, 700 µg, 800 µg, 900 µg, 1000 µg, 1100 µg, 1200 µg, 1300 µg, 1400 µg, 1500 µg, 1600 µg, 1700 µg, 1800 µg, 1900 µg, 2000 µg, 2100 µg, 2200 µg, 2300 µg, 2400 µg, or 2500 µg per dose.

According to embodiments of the application, the Tau phosphopeptide is presented on the surface of the liposomes. According to embodiments of the application, the Tau phosphopeptide comprises the amino acid sequence of one of SEQ ID NOs: 1-3 or 5-12. Preferably, the Tau phosphopeptide consists of the amino acid sequence of one of SEQ ID NO:27 to SEQ ID NO:38. More preferably, the Tau phosphopeptide consists of the amino acid sequence of SEQ ID NO:28.

According to other embodiments of the application, an effective amount of liposomes further comprises a toll-like receptor 4 agonist at an amount of 30 µg to 900 µg, preferably 100 µg to 585 µg, per dose. For example, the effective amount of liposomes can comprise a toll-like receptor 4 agonist at an amount of 30 µg, 50 µg, 100 µg, 150 µg, 200 µg, 250 µg, 300 µg, 330 µg, 360 µg, 390 µg, 420 µg, 450 µg, 480 µg, 500 µg, 520 µg, 540 µg, 560 µg, 580 µg, 600 µg, 700 µg, 800 µg or 900 µg per dose.

According to embodiments of the application, the toll-like receptor 4 comprises 3D-(6-acyl) PHAD®.

According to other embodiments of the application, an effective amount of liposomes further comprises a helper T-cell epitope at an amount of 25 µg to 625 µg, preferably 75 µg to 450 µg, per dose. For example, the effective amount of liposomes can comprise a helper T-cell epitope at an amount of 25 µg, 50 µg, 75 µg, 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg, 500 µg, 525 µg, 550 µg, 575 µg, 600 µg, or 625 µg per dose.

According to other embodiments of the application, an effective amount of liposomes further comprises a helper T-cell epitope at an amount of about 3 nmoles to about 105 nmoles per dose, such as about 4 nmoles, about 5 nmoles, about 6 nmoles, about 7 nmoles, about 8 nmoles, about 9 nmoles, about 10 nmoles, about 15 nmoles, about 20 nmoles, about 25 nmoles, about 30 nmoles, about 35 nmoles, about 40 nmoles, about 45 nmoles, about 50 nmoles, about 55 nmoles, about 60 nmoles, about 65 nmoles, about 70 nmoles, about 75 nmoles, about 80 nmoles, about 85 nmoles, about 90 nmoles, about 95 nmoles, about 100 nmoles, or about 105 nmoles per dose.

According to embodiments of the application, the helper T-cell epitope is a T50 helper T-cell epitope consisting of the amino acid sequence of SEQ ID NO: 13, a T46 helper T-cell epitope consisting of the amino acid sequence of SEQ ID NO: 14, a T48 helper T-cell epitope consisting of the amino acid sequence of SEQ ID NO: 15, a TM helper T-cell epitope consisting of the amino acid sequence of SEQ ID NO: 16, or a T52 helper T-cell epitope consisting of the amino acid sequence of SEQ ID NO: 17, preferably the helper T-cell epitope is a T50 helper T-cell epitope consisting of the amino acid sequence of SEQ ID NO: 13.

In certain embodiments, an effective amount of liposomes further comprises a lipidated CpG oligonucleotide at an amount of 50 µg to 1250 µg, preferably 150 µg to 800 µg, per dose. For example, the effective amount of liposomes can comprise a lipidated CpG oligonucleotide at an amount of 50 µg, 100 µg, 150 µg, 200 µg, 250 µg, 300 µg, 350 µg, 400 µg, 450 µg, 500 µg, 550 µg, 600 µg, 650 µg, 700 µg, 750 µg, 800 µg, 850 µg, 900 µg, 950 µg, 1000 µg, 1050 µg, 1100 µg, 1200 µg, or 1250 µg per dose.

According to embodiments of the application, the lipidated CpG oligonucleotide is a CpG oligonucleotide comprising a nucleotide sequence of one of SEQ ID NOs: 18-22, preferably the lipidated CpG oligonucleotide is a CpG oligonucleotide comprising a nucleotide sequence of SEQ ID NO: 18. According to embodiments of the application, the lipidated CpG oligonucleotide is a CpG oligonucleotide comprising a nucleotide sequence of SEQ ID NO: 18 which has one or more phosphorothioate internucleotide linkages and is covalently linked to cholesterol via a linker comprising polyethylene glycol (PEG).

According to embodiments, the effective amount of liposomes comprise 50 µg, 100 µg, 150 µg, 200 µg, 250 µg, 300 µg, 350 µg, 400 µg, 450 µg, 500 µg, 550 µg, 600 µg, 650 µg, 700 µg, 750 µg, 800 µg, 850 µg, 900 µg, 950 µg, 1000 µg, 1050 µg, 1100 µg, 1200 µg, or 1250 µg per dose of the CpG oligonucleotide covalently linked to cholesterol via the PEG linker.

According to particular embodiments, the human subject is in need of treatment of a neurodegenerative disease, disorder, or condition.

As used herein a "neurodegenerative disease, disorder, or condition" includes any neurodegenerative disease, disorder, or condition known to those skilled in the art in view of the present disclosure. Examples of neurodegenerative diseases, disorders, or conditions include neurodegenerative diseases or disorders caused by or associated with the formation of neurofibrillary lesions, such as Tau-associated diseases, disorders or conditions, referred to as Tauopathies. According to particular embodiments, the neurodegenerative disease, disorder, or condition includes any of the diseases or disorders which show co-existence of Tau and amyloid pathologies including, but not is limited to, Alzheimer's Disease, Parkinson's Disease, Creutzfeldt-Jacob disease, Dementia pugilistica, Down's Syndrome, Gerstmann-Sträussler-Scheinker disease, inclusion body myositis, prion protein cerebral amyloid angiopathy, traumatic brain injury, amyotrophic lateral sclerosis, parkinsonism-dementia complex of Guam, Non-Guamanian motor neuron disease with neurofibrillary tangles, argyrophilic grain dementia, corticobasal degeneration, Dementia Lewy Amyotrophic Lateral sclerosis, diffuse neurofibrillary tangles with calcification, frontotemporal dementia, preferably frontotemporal dementia with parkinsonism linked to chromosome 17 (FTDP-17), frontotemporal lobar dementia, Hallevorden-Spatz disease, multiple system atrophy, Niemann-Pick disease type C, Pick's disease, progressive subcortical gliosis, progressive supranuclear palsy, Subacute sclerosing panencephalitis, Tangle only dementia, Postencephalitic Parkinsonism, Myotonic dystrophy, chronic traumatic encephalopathy (CTE), Primary age-related Tauopathy (PART), cerebral angiopathy or Lewy body dementia (LBD). According to particular embodiments, the neurodegenerative disease, disorder, or condition is Alzheimer's disease or another Tauopathy. According to preferred embodiments, the neurodegenerative disease, disorder, or condition is Alzheimer's Disease.

The clinical course of Alzheimer's Disease can be divided into stages, with progressive patterns of cognitive and functional impairments. The stages can be defined using grading scales known in the art including, e.g., NIA-AA Research Framework. See, e.g., Dubois et al., *Alzheimer's & Dementia* 12 (2016) 292-323, Dubois et al., *Lancet Neurol* 2014; 13: 614-29, Jack et al., *Alzheimer's & Dementia* 14 (2018) 535-562, the content of each of which is hereby incorporated by references in its entirety.

According to preferred embodiments, the neurodegenerative disease, disorder, or condition is early Alzheimer's Disease, mild cognitive impairment (MCI) due to Alzheimer's Disease, mild Alzheimer's Disease, or mild to moderate Alzheimer's Disease.

In some embodiments, the subject in need of a treatment is amyloid positive in the brain but does not yet show significant cognitive impairment. The amyloid deposition in the brain can be detected using methods known in the art, such as PET scan, immunoprecipitation mass spectrometry or other methods.

As used herein, the term "toll-like receptor" or "TLR" refers to a class of pattern recognition receptor (PRR) proteins that play a key role in the innate immune response. TLRs recognize pathogen-associated molecular patterns (PAMPs) from microbial pathogens, such as bacteria, fungi, parasites and viruses, which can be distinguished from host molecules. TLRs are membrane-spanning proteins that typically function as dimers and are expressed by cells involved in the innate immune response, including antigen-presenting dendritic cells and phagocytic macrophages. There are at least ten human TLR family members, TLR1 to TLR10, and at least twelve murine TLR family members, TLR1 to TLR9 and TLR11 to TLR13, and they differ in the types of antigens they recognize. For example, TLR4 recognizes lipopolysaccharides (LPS), a component present in many Gram-negative bacteria, as well as viral proteins, polysaccharide, and endogenous proteins such as low-density lipoprotein, beta-defensins and heat shock protein; and TLR9 is a nucleotide-sensing TLR which is activated by unmethylated cytosine-phosphate-guanine (CpG) single-stranded or double-stranded dinucleotides, which are abundant in prokaryotic genomes but rare in vertebrate genomes. Activation of TLRs leads to a series of signaling events resulting in the production of type I interferons (IFNs), inflammatory cytokines, and chemokines, and the induction of immune responses. Eventually, this inflammation also activates the adaptive immune system, which then results in the clearance of the invading pathogens and the infected cells.

As used herein, the term "agonist" refers to a molecule that binds to one or more TLRs and induces a receptor mediated response. For example, an agonist can induce, stimulate, increase, activate, facilitate, enhance, or up regulate the activity of the receptor. Such activities are referred to as "agonistic activities." For example, a TLR4 or TLR9 agonist can activate or increase cell signaling through the bound receptor. Agonists include, but are not limited to nucleic acids, small molecules, proteins, carbohydrates, lipids or any other molecules that bind or interact with receptors. Agonists can mimic the activity of a natural receptor ligand. Agonists can be homologous to these natural receptor ligands with respect to sequence, conformation, charge or other characteristics such that they can be recognized by the receptors. This recognition can result in physiologic and/or biochemical changes within the cell, such that the cell reacts to the presence of the agonist in the same manner as if the natural receptor ligand were present. According to particular embodiments, the toll-like receptor agonist is at least one of a toll-like receptor 4 agonist and a toll-like receptor 9 agonist.

As used herein, the terms "induce" and "stimulate" and variations thereof refer to any measurable increase in cellular activity. Induction of an immune response can include, for example, activation, proliferation, or maturation of a population of immune cells, increasing the production of a cytokine, and/or another indicator of increased immune function. In certain embodiments, induction of an immune response can include increasing the proliferation of B cells, producing antigen-specific antibodies, increasing the proliferation of antigen-specific T cells, improving dendritic cell antigen presentation and/or an increasing expression of certain cytokines, chemokines and co-stimulatory markers.

As used herein, the term "toll-like receptor 4 agonist" refers to any compound that acts as an agonist of TLR4. Any suitable toll-like receptor 4 agonist known to those skilled in the art in view of the present disclosure can be used in the invention. Examples of toll-like receptor 4 ligand useful for the invention include TLR4 agonist, including, but not limited to, monophosphoryl lipid A (MPLA). As used herein, the term "monophosphoryl lipid A" or "MPLA" refers to a modified form of lipid A, which is the biologically active part of Gram-negative bacterial lipopolysaccharide (LPS) endotoxin. MPLA is less toxic than LPS while maintaining the immunostimulatory activity. As a vaccine adjuvant, MPLA stimulates both cellular and humoral responses to the vaccine antigen. Examples of MPLA include, but are not limited to, 3-O-desacyl-4'-monophosphoryl lipid A, Monophosphoryl Hexa-acyl Lipid A, 3-Deacyl (Synthetic) (also referred to as 3D-(6-acyl) PHAD®), monophosphoryl 3-deacyl lipid A, and structurally related variants thereof. MPLA useful for the invention can be obtained using methods known in the art, or from a commercial source, such as 3D-(6-acyl) PHAD®, PHAD®, PHAD®-504, 3D-PHAD® from Avanti Polar Lipids (Alabaster, Ala., USA) or MPL™ from various commercial sources. According to particular embodiments, the toll-like receptor 4 agonist is MPLA. According to particular embodiments, the liposome comprising a Tau phosphopeptide and a toll-like receptor 4 agonist also comprises a helper T-cell epitope that is capable of binding most or all HLA DR (Human Leukocyte Antigen—antigen D Related) molecules. The helper T-cell epitope is then able to activate CD4$^+$ T-cells and provides essential maturation and survival signals to the Tau-specific B-cells. The Tau liposomes can be used to generate high-quality antibodies against the pTau antigen in homologous or heterologous immunization schemes, with the liposome used in the prime and/or in the boost.

As used herein, the term "helper T-cell epitope" refers to a polypeptide comprising an epitope that is capable of recognition by a helper T-cell. Examples of helper T-cell epitopes include, but are not limited to, tetanus toxoid (e.g., the P2 and P30 epitopes, also named, respectively as T2 and T30), Hepatitis B surface antigen, cholera toxin B, toxoid, diphtheria toxoid, measles virus F protein, *Chlamydia trachomatis* major outer membrane protein, *Plasmodium falciparum* circumsporozite T, *P. falciparum* CS antigen, *Schistosoma mansoni* triose phosphate isomerase, *Bordetella pertussis, Clostridium tetani, Pertusaria trachythallina, Escherichia coli* TraT, and Influenza virus hemagglutinin (HA).

Any suitable helper T-cell epitope known to those skilled in the art can be used in the invention in view of the present disclosure. According to particular embodiments, the helper T-cell epitope comprises at least one amino acid sequence selected from the group consisting of SEQ ID NO:23 to SEQ ID NO:26. Preferably, the helper T-cell epitope comprises two or more of the amino acid sequences of SEQ ID NO:23 to SEQ ID NO:26 fused together via a linker, such as a peptide linker comprising one or more amino acids, e.g., Val (V), Ala (A), Arg (R), Gly (G), Ser (S), Lys (K). The length of the linker can vary, preferably 1-5 amino acids. Preferably, the helper T-cell epitope comprises three or more of the amino acid sequences of SEQ ID NO:23 to SEQ ID NO:26 fused together via one or more linkers selected from the group consisting of VVR, GS, RR, RK. The helper T-cell epitope can have its C-terminus amidated.

According to embodiments of the application, the helper T-cell epitopes can be incorporated on the liposomal surface, e.g. anchored by a covalently bound hydrophobic moiety wherein said hydrophobic moiety is an alkyl group, a fatty acid, a triglyceride, diglyceride, steroid, sphingolipid, glycolipid or a phospholipid, particularly an alkyl group or a fatty acid, particularly with a carbon backbone of at least 3 carbon atoms, particularly of at least 4 carbon atoms, particularly of at least 6 carbon atoms, particularly of at least 8 carbon atoms, particularly of at least 12 carbon atoms, particularly of at least 16 carbon atoms. In one embodiment of the invention, the hydrophobic moiety is palmitic acid. Alternatively, the helper T-cell epitopes can be encapsulated in the liposomes. According to particular embodiments, the helper T-cell epitope is encapsulated in the liposome.

The helper T-cell epitope can be modified for its desired location in the liposomes using methods known in the art in view of the present disclosure. According to particular embodiments, the helper T-cell epitope useful for the invention comprises an amino acid sequence of one of SEQ ID NO:39 to SEQ ID NO:44. Preferably, the helper T cell epitope consists of an amino acid sequence selected from the group consisting of SEQ ID NO:13 to SEQ ID NO:17.

According to particular embodiments, the liposome comprising a Tau phosphopeptide and a toll-like receptor 4 agonist also comprises a toll-like receptor 9 agonist. As used herein, the term "toll-like receptor 9 agonist" refers to any compound that acts as an agonist of TLR9. Any suitable toll-like receptor 9 agonist known to those skilled in the art in view of the present disclosure can be used in the invention. Examples of toll-like receptor 9 ligand useful for the invention include TLR9 agonist including, but not limited to, CpG oligonucleotides.

As used herein, the term "CpG oligonucleotide", "CpG oligodeoxynucleotide" or "CpG ODN" refers to an oligonucleotide comprising at least one CpG motif. As used herein, "oligonucleotide," "oligodeoxynucleotide" or "ODN" refers to a polynucleotide formed from a plurality of linked nucleotide units. Such oligonucleotides can be obtained from existing nucleic acid sources or can be produced by synthetic methods. As used herein, the term "CpG motif" refers to a nucleotide sequence which contains unmethylated cytosine-phosphate-guanine (CpG) dinucleotides (i.e., a cytosine (C) followed by a guanine (G)) linked by a phosphate bond or a phosphodiester backbone or other internucleotide linkages.

According to particular embodiments, the CpG oligonucleotide is lipidated, i.e. conjugated (covalently linked) to a lipid moiety.

As used herein, a "lipid moiety" refers to a moiety containing a lipophilic structure. Lipid moieties, such as an alkyl group, a fatty acid, a triglyceride, diglyceride, steroid, sphingolipid, glycolipid or a phospholipid, particularly a sterol such as cholesterol, or fatty acids, when attached to highly hydrophilic molecules, such as nucleic acids, can substantially enhance plasma protein binding and consequently circulation half-life of the hydrophilic molecules. In addition, binding to certain plasma proteins, such as lipoproteins, has been shown to increase uptake in specific tissues expressing the corresponding lipoprotein receptors (e.g., LDL-receptor HDL-receptor or the scavenger receptor SR-B1). In particular, a lipid moiety conjugated to the phosphopeptides and/or CpG oligonucleotide allows anchoring the said peptides and/or oligonucleotides into the membrane of a liposome via a hydrophobic moiety.

According to particular embodiments, in view of the present disclosure, the CpG oligonucleotide can comprise any suitable internucleotide linkages.

As used herein, the term "internucleotide linkage" refers to a chemical linkage to join two nucleotides through their sugars consisting of a phosphorous atom and a charged or neutral group between adjacent nucleosides. Examples of internucleotide linkage include phosphodiester (po), phosphorothioate (ps), phosphorodithioate (ps2), methylphosphonate (mp), and methylphosphorothioate (rp). Phosphorothioate, phosphorodithioate, methylphosphonate and methylphosphorothioate are stabilizing internucleotide linkages, while phosphodiester is a naturally-occurring internucleotide linkage. Oligonucleotide phosphorothioates are typically synthesized as a random racemic mixture of Rp and Sp phosphorothioate linkages.

Any suitable CpG oligonucleotide known to those skilled in the art can be used in the invention in view of the present disclosure. Examples of such CpG oligonucleotides include, but are not limited to CpG2006 (also known as CpG 7909) (SEQ ID NO: 18), CpG 1018 (SEQ ID NO: 19), CpG2395 (SEQ ID NO: 20), CpG2216 (SEQ ID NO: 21) or CpG2336 (SEQ ID NO: 22).

A CpG oligonucleotide can be lipidated using methods known in the art in view of the present disclosure. In some embodiments, the CpG oligonucleotide is covalently linked to a cholesterol molecule directly. In some embodiments, the 3' terminus of a CpG oligonucleotide is covalently linked to a cholesterol molecule through a phosphate bond, optionally via a PEG linker. In some embodiments, the 5' terminus of a CpG oligonucleotide is covalently linked to a cholesterol molecule through a phosphate bond, optionally via a PEG linker. Other lipophilic moiety can also be covalently linked to the 5' or 3' terminus of a CpG oligonucleotide. For example a CpG oligonucleotide can be covalently linked to a lipid anchor of the same length as the phospholipids from liposome: one palmitic acid chain (using Pal-OH or similar, activated for coupling) or two palmitic acids (e.g., using 1,2-dipalmitoyl-sn-glycero-3-phosphoethanolamine-N-(succinyl) or similar, activated for coupling), optionally via a PEG linker. See, e.g., relevant disclosure in U.S. Pat. No. 7,741,297, the content of which is incorporated herein by reference. The length of PEG can vary, from example, from 1 to 5 PEG units.

Other linkers can also be used to covalently connect a CpG oligonucleotide to a lipophilic moiety (such as a cholesterol molecule), examples of which include, but are not limited to an alkyl spacer having 3 to 12 carbons. A short linker compatible with oligonucleotide chemistry is needed as aminodiol. In some embodiment, no linker is used for the covalent bonding. See e.g., Ries et al., "Convenient synthesis and application of versatile nucleic acid lipid membrane anchors in the assembly and fusion of liposomes, *Org. Biomol. Chem.*, 2015, 13, 9673, the relevant disclosure of which is incorporated herein by reference.

According to particular embodiments, lipidated CpG oligonucleotide useful for the invention comprises a nucleotide sequence selected from the group consisting of SEQ ID NO:18 to SEQ ID NO:22, wherein the nucleotide sequence comprises one or more phosphorothioate internucleotide linkages, and the nucleotide sequence is covalently linked to at least one cholesterol via a linker. According to preferred embodiments, the lipidated CpG oligonucleotide comprises a nucleotide sequence of SEQ ID NO: 18, has one or more phosphorothioate internucleotide linkages, and is covalently linked to cholesterol. Any suitable linkers can be used to covalently link a CpG oligonucleotide to a cholesterol molecule. Preferably, the linker comprises polyethylene glycol (PEG).

According to particular embodiments, the liposome further comprises one or more lipids selected from the group consisting of 1,2-dimyristoyl-sn-glycero-3-phosphocholine (DMPC), 1,2-dimyristoyl-sn-glycero-3-phosphoryl-3'-rac-glycerol (DMPG), and cholesterol.

According to particular embodiments, the liposome further comprises a buffer. Any suitable buffer known to those skilled in the art in view of the present disclosure can be used in the invention. In one embodiment, the liposome comprises a phosphate-buffered saline. According to particular embodiments, the buffer comprises histidine and sucrose.

An exemplary liposome used in the present invention comprises a Tau tetrapalmitoylated phosphopeptide (pTau Peptide T3, SEQ ID NO: 28) that is presented on the surface of the liposome via two palmitic acids at each terminus of the Tau peptide; A TLR-9 ligand comprising lipidated CpG (Adjuvant CpG7909-Chol; SEQ ID NO: 18) incorporated into the liposome membrane via a cholesterol molecule that is covalently linked to the CpG via a PEG linker; a TLR-4 ligand (Monophosphoryl lipid A (e.g., 3D-(6-acyl) PHAD®)) incorporated into the membrane; an encapsulated helper T-cell epitope (PAN-DR binder T50; SEQ ID NO: 13); and 1,2-dimyristoyl-sn-glycero-3-phospho-choline (DMPC), 1,2-dimyristoyl-sn-glycero-3-[phospho-rac-(1-glycerol)] sodium salt (DMPG) and cholesterol as lipid components of the liposome.

Liposomes of the invention can be made using methods known in the art in view of the present disclosure. The optimal ratios of each component of the liposomes can be determined by techniques known to those skilled in the art in view of the present disclosure.

The liposomes can be administered by suitable means for prophylactic and/or therapeutic treatment. According to preferred embodiments, the liposomes are administered by subcutaneous or intramuscular injection. Intramuscular injection is most typically performed in the arm or leg muscles.

In one general aspect, the invention relates to pharmaceutical compositions comprising a therapeutically effective amount of liposome, together with a pharmaceutically acceptable excipient and/or carrier. Pharmaceutically acceptable excipients and/or carriers are well known in the art (see Remington's Pharmaceutical Science (15th ed.), Mack Publishing Company, Easton, Pa., 1980). The preferred formulation of the pharmaceutical composition depends on the intended mode of administration and therapeutic application. The compositions can include pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or non-toxic, non-therapeutic, non-immunogenic stabilizers, and the like. It will be understood that the characteristics of the carrier, excipient or diluent will depend on the route of administration for a particular application.

The target antigen for the vaccine is located in the brain, and the brain is separated from the circulation by a specialized cellular structure called the blood-brain barrier (BBB). The BBB restricts passage of substances from the circulation into the brain. This prevents the entry of toxins, microbes, etc. into the central nervous system. The BBB also has the potentially less desirable effect of preventing the efficient entry of immune mediators (such as antibodies) into the interstitial and cerebrospinal fluid that surrounds the brain.

Approximately 0.1% of antibodies that are present in the systemic circulation cross the BBB and enter the brain. This suggests that systemic titers induced by a vaccine targeting a CNS antigen must be at least 1000 times greater than the minimal effective titer to be efficacious in the brain. The minimum titers of antibodies in serum which are needed to trigger efficacy are not readily apparent. Additionally, not only the quantity but also the quality of the immune response (e.g. avidity) must be considered for a safe and effective immunotherapy targeting a CNS disorder, such as a neurodegenerative disease, disorder, or condition.

According to particular embodiments, the pharmaceutical compositions of the present invention therefore further comprise one or more suitable adjuvants to achieve the desired immune response in the subject. Suitable adjuvants can be administered before, after, or concurrent with administration of the liposome. Preferred adjuvants augment the intrinsic response to an immunogen without causing conformational changes in the immunogen that affect the qualitative form of the response. Examples of adjuvants are the aluminum salts (alum), such as aluminum hydroxide, aluminum phosphate, and aluminum sulfate. Such adjuvants can be used with or without other specific immunostimulating agents, such as MPLA Class (3 De-O-acylated monophosphoryl lipid A (MPL'), monophosphoryl hexa-acyl Lipid A 3-deacyl synthetic (3D-(6-acyl) PHAD®, PHAD™, PHAD®-504, 3D-PHAD®) lipid A), polymeric or monomeric amino acids, such as polyglutamic acid or polylysine. Such adjuvants can be used with or without other specific immunostimulating agents, such as muramyl peptides (e.g., N-acetylmuramyl-L-threonyl-D-isoglutamine (thr-MDP), N-acetylnormuramyl-L-alanyl-D-isoglutamine (nor-MDP), N-acetylmuramyl-L-alanyl-D-isoglutaminyl-L-alanine-2-(1'-2' dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) Theramide™), or other bacterial cell wall components. Oil-in-water emulsions include MF59 (see WO 90/14837), containing 5% Squalene, 0.5% Tween 80, and 0.5% Span 85 (optionally containing various amounts of MTP-PE) formulated into submicron particles using a microfluidizer; SAF, containing 10% Squalene, 0.4% Tween 80, 5% pluronic-blocked polymer L121, and thr-MDP, either microfluidized into a submicron emulsion or vortexed to generate a larger particle size emulsion; and the Ribi™ adjuvant system (RAS) (Ribi ImmunoChem, Hamilton, Mont.) 0.2% Tween 80, and one or more bacterial cell wall components selected from the group consisting of monophosphoryl lipid A (MPL™), trehalose dimycolate (TDM), and cell wall skeleton (CWS), preferably MPL™+CWS (Detox™). Other adjuvants include Complete Freund's Adjuvant (CFA), and cytokines, such as interleukins (IL-1, IL-2, and IL-12), macrophage colony stimulating factor (M-CSF), and tumor necrosis factor (TNF).

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

The timing of administrations can vary significantly from once a day, to once a year, to once a decade. A typical regimen consists of an immunization followed by booster injections at time intervals, such as 1 to 24 week intervals. Another regimen consists of an immunization followed by booster injections 1, 2, 4, 6, 8, 10 and 12 months later. Another regimen entails an injection every two months for life. Alternatively, booster injections can be on an irregular basis as indicated by monitoring of immune response.

It is readily appreciated by those skilled in the art that the regimen for the priming and boosting administrations can be adjusted based on the measured immune responses after the administrations. For example, the boosting compositions are generally administered weeks or months after administration of the priming composition, for example, about 1 week, or 2 weeks, or 3 weeks, or 4 weeks, or 8 weeks, or 16 weeks, or 20 weeks, or 24 weeks, or 28 weeks, or 32 weeks, or 36 weeks, or 40 weeks, or 44 weeks, or 48 weeks, or 52 weeks, or 56 weeks, or 60 weeks, or 64 weeks, or 68 weeks, or 72 weeks, or 76 weeks, or one to two years after administration of the priming composition.

According to particular aspects, one or more boosting immunizations can be administered. The antigens in the respective priming and boosting compositions, however many boosting compositions are employed, need not be identical, but should share antigenic determinants or be substantially similar to each other.

Pharmaceutical compositions of the present invention can be formulated according to methods known in the art in view of the present disclosure. The optimal ratios of each component in the compositions can be determined by techniques known to those skilled in the art in view of the present disclosure.

In a preferred embodiment of the present invention, administration of a Tau peptide, via administration of a pharmaceutical composition according to an embodiment of the invention, induces an active immune response in the subject to the Tau peptide and to the pathological form of Tau, thereby facilitating the clearance of related Tau aggregates, slowing the progression of Tau-pathology related behavior and/or treating the underlying Tauopathy.

Tau is a human "self" protein. This means that, in principle, all lymphocytes bearing a receptor specific for tau should have been deleted during development (central tolerance) or rendered unresponsive by a peripheral tolerance mechanism. This problem has proved to be a significant roadblock to the development of vaccines against self or "altered self" proteins (e.g. tumor antigens). Generating high-quality antibodies against an antigen (self or infectious) requires the action of not only B lymphocytes, which produce the antibody, but also of $CD4^+$ T "helper" lymphocytes. $CD4^+$ T-cells provide critical survival and maturation signals to B lymphocytes, and $CD4^+$ T-cell deficient animals are profoundly immunosuppressed. $CD4^+$ T-cells are also subject to tolerance mechanisms, and an additional roadblock to generating strong anti-self (e.g., anti-tau) antibody responses is that tau-reactive $CD4^+$ T-cells are also likely to be rare to non-existent in the human/animal repertoire.

In accordance with this aspect of the present invention, an immune response involves the development of a beneficial humoral (antibody mediated) response directed against the Tau peptide and a cellular (mediated by antigen-specific T cells or their secretion products) response directed against the T-cell epitope or the immunogenic carrier.

As used herein, a Tau-pathology related behavioral phenotype includes, without limitation, cognitive impairments, early personality change and disinhibition, apathy, abulia, mutism, apraxia, perseveration, stereotyped movements/behaviors, hyperorality, disorganization, inability to plan or organize sequential tasks, selfishness/callousness, antisocial traits, a lack of empathy, halting, agrammatic speech with frequent paraphasic errors but relatively preserved comprehension, impaired comprehension and word-finding deficits, slowly progressive gait instability, retropulsions, freezing, frequent falls, non-levodopa responsive axial rigidity, supranuclear gaze palsy, square wave jerks, slow vertical saccades, pseudobulbar palsy, limb apraxia, dystonia, cortical sensory loss, and tremor.

In carrying out the methods of the present invention, according to particular embodiments of the invention, it is preferable to select a subject having or at risk of having Alzheimer's disease or other Tauopathy, a subject having Tau aggregates in the brain, or a subject exhibiting a tangle related behavioral phenotype prior to administering the immunogenic peptides or antibodies of the present invention. Subjects amenable to treatment include individuals at risk of disease but not showing symptoms, as well as patients presently showing symptoms. In the case of Alzheimer's disease, virtually anyone is at risk of suffering from Alzheimer's disease. Therefore, the present methods can be administered prophylactically to the general population without the need for any assessment of the risk of the subject patient. The present methods are especially useful for individuals who have a known genetic risk of Alzheimer's disease. Such individuals include those having relatives who have experienced the disease, and those whose risk is determined by analysis of genetic or biochemical markers. In preferred embodiments, the subject is in need of a treatment of Alzheimer's Disease, preferably early Alzheimer's Disease, mild cognitive impairment (MCI) due to Alzheimer's Disease, mild Alzheimer's Disease, or mild to moderate Alzheimer's Disease.

In asymptomatic patients, treatment can begin at any age (e.g., 10, 20, 30 years of age). Usually, however, it is not necessary to begin treatment until a patient reaches 40, 50, 60, or 70 years of age. Treatment typically entails multiple dosages over a period of time. Treatment can be monitored by assaying antibody, or activated T-cell or B-cell responses to the therapeutic agent over time. If the response decreases, a booster dosage is indicated.

In prophylactic applications, pharmaceutical compositions containing the Tau peptides are administered to a patient susceptible to, or otherwise at risk of, Alzheimer's disease or other Tauopathy in an amount sufficient to eliminate or reduce the risk, lessen the severity, or delay the outset of the disease, including biochemical, histologic and/or behavioral symptoms of the disease, its complications and intermediate pathological phenotypes presented during development of the disease. In therapeutic applications, pharmaceutical compositions containing a Tau peptide are administered to a patient suspected of, or already suffering from, such a disease in an amount sufficient to cure, or at least partially arrest, the symptoms of the disease (biochemical, histologic and/or behavioral), including its complications and intermediate pathological phenotypes in development of the disease.

The composition can, if desired, be presented in a kit, pack or dispenser, which can contain one or more unit dosage forms containing the active ingredient. The kit, for example, can comprise metal or plastic foil, such as a blister pack. The kit, pack, or dispenser can be accompanied by instructions for administration.

Embodiments

The invention provides also the following non-limiting embodiments.

Embodiment 1 is a method of inducing anti-phosphorylated Tau antibodies without inducing a severe adverse event in a subject in need thereof, comprising administering to the subject an effective amount of liposomes comprising a Tau phosphopeptide comprising an amino acid sequence selected from the group consisting of SEQ ID NO:1 to SEQ ID NO:3 and SEQ ID NO:5 to SEQ ID NO:12 at an amount of about 25 nmoles to about 750 nmoles per dose, preferably about 90 nmoles to about 715 nmoles per dose, about 90 nmoles to about 535 nmoles per dose or about 90 nmoles to about 275 nmoles per dose, such as about 25 nmoles, about 30 nmoles, about 35 nmoles, about 40 nmoles, about 45 nmoles, about 50 nmoles, about 55 nmoles, about 60 nmoles, about 65 nmoles, about 70 nmoles, about 75 nmoles, about 80 nmoles, about 85 nmoles, about 90 nmoles, about 95 nmoles, about 100 nmoles, about 125 nmoles, about 150 nmoles, about 175 nmoles, about 200 nmoles, about 225 nmoles, about 250 nmoles, about 275 nmoles, about 300 nmoles, about 325 nmoles, about 350 nmoles, about 375 nmoles, about 400 nmoles, about 425 nmoles, about 450 nmoles, about 475 nmoles, about 500 nmoles, about 525 nmoles, about 550 nmoles, about 575 nmoles, about 600 nmoles, about 625 nmoles, about 650 nmoles, about 675 nmoles, about 700 nmoles, about 725 nmoles, about 750 nmoles, or any value in between, per dose, and a toll-like receptor 4 agonist, wherein the Tau phosphopeptide is presented on the surface of the liposome.

Embodiment 1a is a method of inducing anti-phosphorylated Tau antibodies without inducing encephalitis in a subject in need thereof, comprising administering to the subject an effective amount of liposomes comprising 100 µg to 2500 µg, preferably 300 µg to 2400 µg, 300 µg to 1800 µg, or 300 µg to 900 µg per dose, such as 100 µg, 150 µg, 200 µg, 250 µg, 300 µg, 400 µg, 500 µg, 600 µg, 700 µg, 800 µg, 900 µg, 1000 µg, 1100 µg, 1200 µg, 1300 µg, 1400 µg, 1500 µg, 1600 µg, 1700 µg, 1800 µg, 1900 µg, 2000 µg, 2100 µg, 2200 µg, 2300 µg, 2400 µg, 2500 µg, or any value in between, per dose, of a tetrapalmitoylated Tau phosphopeptide presented on the surface of the liposomes and a toll-like receptor 4 agonist, wherein the Tau phosphopeptide comprises an amino acid sequence selected from the group consisting of SEQ ID NO:1 to SEQ ID NO:3 and SEQ ID NO:5 to SEQ ID NO:12.

Embodiment 2 is the method of Embodiment 1 or 1a, wherein the Tau phosphopeptide consists of an amino acid sequence selected from the group consisting of SEQ ID NO:27 to SEQ ID NO:29 and SEQ ID NO:31 to SEQ ID NO:38.

Embodiment 3a is the method of any of Embodiments 1 to 2, wherein the Tau phosphopeptide consists of the amino acid sequence of SEQ ID NO:27.

Embodiment 3b is the method of any of Embodiments 1 to 2, wherein the Tau phosphopeptide consists of the amino acid sequence of SEQ ID NO:28.

Embodiment 3c is the method of any of Embodiments 1 to 2, wherein the Tau phosphopeptide consists of the amino acid sequence of SEQ ID NO:29.

Embodiment 3d is the method of any of Embodiments 1 to 2, wherein the Tau phosphopeptide consists of the amino acid sequence of SEQ ID NO:31.

Embodiment 3e is the method of any of Embodiments 1 to 2, wherein the Tau phosphopeptide consists of the amino acid sequence of SEQ ID NO:32.

Embodiment 3f is the method of any of Embodiments 1 to 2, wherein the Tau phosphopeptide consists of the amino acid sequence of SEQ ID NO:33.

Embodiment 3g is the method of any of Embodiments 1 to 2, wherein the Tau phosphopeptide consists of the amino acid sequence of SEQ ID NO:34.

Embodiment 3h is the method of any of Embodiments 1 to 2, wherein the Tau phosphopeptide consists of the amino acid sequence of SEQ ID NO:35.

Embodiment 3i is the method of any of Embodiments 1 to 2, wherein the Tau phosphopeptide consists of the amino acid sequence of SEQ ID NO:36.

Embodiment 3j is the method of any of Embodiments 1 to 2, wherein the Tau phosphopeptide consists of the amino acid sequence of SEQ ID NO:37.

Embodiment 3k is the method of any of Embodiments 1 to 2, wherein the Tau phosphopeptide consists of the amino acid sequence of SEQ ID NO:38.

Embodiment 4 is the method of any of Embodiments 1 to 3k, wherein the liposomes are administered subcutaneously.

Embodiment 5 is the method of any of Embodiments 1 to 3k, wherein the liposomes are administered intramuscularly.

Embodiment 6 is the method of any one of Embodiments 1 to 5, further comprising administering to the subject a second dose of the effective amount of the liposomes 1 to 24 weeks after the initial administration.

Embodiment 7 is the method of any one of Embodiments 1 to 6, wherein the liposome further comprises at least one of a helper T-cell epitope and a lipidated CpG oligonucleotide, preferably a helper T-cell epitope and a lipidated CpG oligonucleotide.

Embodiment 7a is the method of Embodiment 7, wherein the effective amount of liposomes comprises the toll-like receptor 4 agonist at an amount of 30 µg to 900 µg, preferably 100 µg to 585 µg, such as 30 µg, 50 µg, 100 µg, 150 µg, 200 µg, 250 µg, 300 µg, 330 µg, 360 µg, 390 µg, 420 µg, 450 µg, 480 µg, 500 µg, 520 µg, 540 µg, 560 µg, 580 µg, 600 µg, 700 µg, 800 µg or 900 µg, or any value in between, per dose.

Embodiment 7b is the method of Embodiment 7 or 7a, wherein the toll-like receptor 4 agonist is monophosphoryl hexa-acyl Lipid A, 3-deacyl.

Embodiment 7c is the method of any one of Embodiments 7-7b, wherein the effective amount of liposomes comprises the helper T-cell epitope at an amount of 25 µg to 625 µg, preferably 75 µg to 450 µg, such as 25 µg, 50 µg, 75 µg, 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg, 500 µg, 525 µg, 550 µg, 575 µg, 600 µg, or 625 µg, or any value in between, per dose.

Embodiment 7d is the method of any one of Embodiments 7-7c, wherein the helper T-cell epitope is a T50 helper T-cell epitope consisting of the amino acid sequence of SEQ ID NO: 13, a T46 helper T-cell epitope consisting of the amino acid sequence of SEQ ID NO: 14, a T48 helper T-cell epitope consisting of the amino acid sequence of SEQ ID NO: 15, a T51 helper T-cell epitope consisting of the amino acid sequence of SEQ ID NO: 16, or a T52 helper T-cell epitope consisting of the amino acid sequence of SEQ ID NO: 17.

Embodiment 7e is the method of Embodiment 7d, wherein the helper T-cell epitope is a T50 helper T-cell epitope consisting of the amino acid sequence of SEQ ID NO: 13.

Embodiment 7f is the method of any one of Embodiments 7-7e, wherein the effective amount of liposomes comprises the lipidated CpG oligonucleotide at an amount of 50 µg to 1250 ng, preferably 150 µg to 800 µg, such as 50 µg, 100 µg, 150 µg, 200 µg, 250 µg, 300 µg, 350 µg, 400 µg, 450 µg, 500 µg, 550 µg, 600 µg, 650 µg, 700 µg, 750 µg, 800 µg, 850 µg, 900 µg, 950 µg, 1000 µg, 1050 µg, 1100 µg, 1200 µg, or 1250 ng, or any value in between, per dose.

Embodiment 8 is the method of any one of Embodiments 7-7f, wherein the lipidated CpG oligonucleotide has a nucleotide sequence selected from the group consisting of SEQ ID NO:18 to SEQ ID NO:22.

Embodiment 9a is the method of Embodiment 8, wherein the CpG oligonucleotide has the nucleotide sequence of SEQ ID NO:18.

Embodiment 9b is the method of Embodiment 8, wherein the CpG oligonucleotide has the nucleotide sequence of SEQ ID NO:19.

Embodiment 9c is the method of Embodiment 8, wherein the CpG oligonucleotide has the nucleotide sequence of SEQ ID NO:20.

Embodiment 9d is the method of Embodiment 8, wherein the CpG oligonucleotide has the nucleotide sequence of SEQ ID NO:21.

Embodiment 9e is the method of Embodiment 8, wherein the CpG oligonucleotide has the nucleotide sequence of SEQ ID NO:22.

Embodiment 10 is the method of any one of Embodiments 8 to 9e, wherein the CpG oligonucleotide has one or more phosphorothioate internucleotide linkages.

Embodiment 11 is the method of any of Embodiments 8 to 10, wherein the CpG oligonucleotide is covalently linked to at least one lipophilic group.

Embodiment 11a is the method of any of Embodiments 8 to 10, wherein the CpG oligonucleotide is covalently linked to at least one lipophilic group via a PEG linker.

Embodiment 12 is the method of Embodiment 11 or 11a, wherein the CpG oligonucleotide is covalently linked to a cholesterol group.

Embodiment 12a is the method of Embodiment 12, wherein the CpG oligonucleotide is covalently linked to a cholesterol group via a PEG linker.

Embodiment 13 is the method of any one of Embodiments 1 to 12a, wherein the liposome further comprises one or more lipids selected from the group consisting of 1,2-dimyristoyl-sn-glycero-3-phosphocholine (DMPC), 1,2-dimyristoyl-sn-glycero-3-phosphoryl-3'-rac-glycerol (DMPG), and cholesterol.

Embodiment 14 is the method of any one of Embodiments 1 to 13, wherein the helper T-cell epitope comprises at least one amino acid sequence selected from the group consisting of SEQ ID NO:23 to SEQ ID NO:26.

Embodiment 15 is the method of Embodiment 14, wherein the helper T-cell epitope comprises the amino acid sequence of SEQ ID NO:23, SEQ ID NO:24, and SEQ ID NO:25.

Embodiment 16 is the method of Embodiment 14 or 15, wherein the helper T-cell epitope comprises an amino acid sequence selected from the group consisting of SEQ ID NOs:13-17 and 39-44.

Embodiment 17 is the method of any one of Embodiments 1 to 16, wherein the toll-like receptor 4 agonist is monophosphoryl lipid A (MPLA).

Embodiment 18 is a method of inducing anti-phosphorylated Tau antibodies without inducing a severe adverse event in a subject in need thereof, comprising administering to the subject an effective amount of liposomes comprising about 25 nmoles to about 750 nmoles, preferably about 90 nmoles to about 715 nmoles per dose or about 90 nmoles to about 535 nmoles per dose or about 90 nmoles to about 275 moles per dose, such as such as about 25 nmoles, about 30 nmoles, about 35 nmoles, about 40 nmoles, about 45 nmoles, about 50 nmoles, about 55 nmoles, about 60 nmoles, about 65 nmoles, about 70 nmoles, about 75 nmoles, about 80 nmoles, about 85 nmoles, about 90 nmoles, about 95 nmoles, about 100 nmoles, about 125 nmoles, about 150 nmoles, about 175 nmoles, about 200 nmoles, about 225 nmoles, about 250 nmoles, about 275 nmoles, about 300 nmoles, about 325 nmoles, about 350 nmoles, about 375 nmoles, about 400 nmoles, about 425 nmoles, about 450 nmoles, about 475 nmoles, about 500 nmoles, about 525 nmoles, about 550 nmoles, about 575 nmoles, about 600 nmoles, about 625 nmoles, about 650 nmoles, about 675 nmoles, about 700 nmoles, about 725 nmoles, or any value in between, per dose, or 300 μg to 2400 μg, such as 300 μg to 1800 μg, or 300 μg to 900 μg per dose, such as 100 μg, 150 μg, 200 μg, 250 μg, 300 μg, 400 μg, 500 μg, 600 μg, 700 μg, 800 μg, 900 μg, 1000 μg, 1100 μg, 1200 μg, 1300 μg, 1400 μg, 1500 μg, 1600 μg, 1700 μg, 1800 ng, 1900 ng, 2000 ng, 2100 ng, 2200 ng, 2300 ng, 2400 μg, 2500 μg, or any value in between, per dose of a tetrapalmitoylated Tau phosphopeptide presented on the surface of the liposomes, wherein the Tau phosphopeptide comprises an amino acid sequence selected from the group consisting of SEQ ID NO:1 to SEQ ID NO:3 and SEQ ID NO:5 to SEQ ID NO:12, and the liposomes further comprises monophosphoryl lipid A (MPLA), 1,2-dimyristoyl-sn-glycero-3-phosphocholine (DMPC), 1,2-dimyristoyl-sn-glycero-3-phosphoryl-3'-rac-glycerol (DMPG), cholesterol, and a buffer.

Embodiment 18a is a method of inducing anti-phosphorylated Tau antibodies without inducing encephalitis in a subject in need thereof, comprising administering to the subject an effective amount of liposomes comprising about 25 nmoles to about 750 nmoles, preferably about 90 nmoles to about 715 nmoles per dose or about 90 nmoles to about 535 nmoles per dose or about 90 nmoles to about 275 nmoles per dose, such as such as about 25 nmoles, about 30 nmoles, about 35 nmoles, about 40 nmoles, about 45 nmoles, about 50 nmoles, about 55 nmoles, about 60 nmoles, about 65 nmoles, about 70 nmoles, about 75 nmoles, about 80 nmoles, about 85 nmoles, about 90 nmoles, about 95 nmoles, about 100 nmoles, about 125 nmoles, about 150 nmoles, about 175 nmoles, about 200 nmoles, about 225 nmoles, about 250 nmoles, about 275 nmoles, about 300 nmoles, about 325 nmoles, about 350 nmoles, about 375 nmoles, about 400 nmoles, about 425 nmoles, about 450 nmoles, about 475 nmoles, about 500 nmoles, about 525 nmoles, about 550 nmoles, about 575 nmoles, about 600 nmoles, about 625 nmoles, about 650 nmoles, about 675 nmoles, about 700 nmoles, about 725 nmoles, about 750 nmoles, or any value in between, per dose, or 100 μg to 2500 μg, or 300 μg to 2400 μg, such as 300 μg to 1800 μg, or 300 μg to 900 μg per dose, e.g., 100 μg, 150 μg, 200 μg, 250 μg, 300 μg, 400 μg, 500 μg, 600 μg, 700 μg, 800 μg, 900 μg, 1000 μg, 1100 μg, 1200 μg, 1300 μg, 1400 μg, 1500 μg, 1600 μg, 1700 μg, 1800 μg, 1900 μg, 2000 μg, 2100 μg, 2200 μg, 2300 μg, 2400 μg, 2500 μg, or any value in between, per dose of a tetrapalmitoylated Tau phosphopeptide presented on the surface of the liposomes, wherein the Tau phosphopeptide comprises an amino acid sequence selected from the group consisting of SEQ ID NO:1 to SEQ ID NO:3 and SEQ ID NO:5 to SEQ ID NO:12, and the liposomes further comprises monophosphoryl lipid A (MPLA), 1,2-dimyristoyl-sn-glycero-3-phosphocholine (DMPC), 1,2-dimyristoyl-sn-glycero-3-phosphoryl-3'-rac-glycerol (DMPG), cholesterol, and a buffer.

Embodiment 19 is the method of Embodiment 18 or 18a, wherein the liposomes further comprise a helper T-cell epitope and a CpG oligonucleotide covalently linked to a cholesterol group.

Embodiment 19a is the method of Embodiment 19, wherein the CpG oligonucleotide is covalently linked to a cholesterol group via a PEG linker.

Embodiment 19b is the method of Embodiment 19 or 19a, wherein the helper T-cell epitope comprises the amino acid sequences of SEQ ID NO:23, SEQ ID NO:24, and SEQ ID NO:25.

Embodiment 19c is the method of Embodiment 19 or 19a, wherein the helper T-cell epitope comprises an amino acid sequence selected from the group consisting of SEQ ID NOs:13-17 and 39-44.

Embodiment 19d is the method of Embodiment 19 or 19a, wherein the helper T-cell epitope comprises the amino acid sequence of SEQ ID NO: 39.

Embodiment 19e is the method of Embodiment 19 or 19a, wherein the helper T-cell epitope comprises the amino acid sequence of SEQ ID NO: 13.

Embodiment 19f is the method of any one of Embodiments 19 to 19e, wherein the CpG oligonucleotide has the nucleotide sequence of SEQ ID NO:18.

Embodiment 19g is the method of any one of Embodiments 19 to 19e, wherein the CpG oligonucleotide has the nucleotide sequence of SEQ ID NO:19.

Embodiment 20a is the method of any one of Embodiments 18 to 19g, wherein the Tau phosphopeptide consists of the amino acid sequence of SEQ ID NO:27.

Embodiment 20b is the method of any one of Embodiments 18 to 19g, wherein the Tau phosphopeptide consists of the amino acid sequence of SEQ ID NO:28.

Embodiment 20c is the method of any one of Embodiments 18 to 19g, wherein the Tau phosphopeptide consists of the amino acid sequence of SEQ ID NO:29.

Embodiment 21a is the method of any one of Embodiments 18 to 20c, wherein the buffer comprises a phosphate buffer.

Embodiment 21b is the method of any one of Embodiments 18 to 20c, wherein the buffer comprises at least one of histidine and sucrose.

Embodiment 22a is the method of any one of Embodiments 18 to 21b, wherein the MPLA comprises monophosphoryl lipid A (e.g., 3D-(6-acyl) PHAD®).

Embodiment 23 is the method of any one of Embodiments 1 to 22a, wherein the subject is in need of a treatment of Alzheimer's Disease.

Embodiment 24 is the method of any one of Embodiments 1 to 22a, wherein the subject is in need of a prevention of Alzheimer's Disease.

Embodiment 25 is the method of Embodiment 23, wherein the subject is in need of a treatment of early Alzheimer's Disease, mild cognitive impairment (MCI) due to Alzheimer's Disease, mild Alzheimer's Disease or mild to moderate Alzheimer's Disease.

Embodiment 26 is the method of any one of Embodiments 1 to 25, wherein the subject is a human subject.

EXAMPLES

The following examples of the invention are to further illustrate the nature of the invention. It should be understood that the following examples do not limit the invention and that the scope of the invention is to be determined by the appended claims.

The experimental methods used in the following examples, unless otherwise indicated, are all ordinary methods. The reagents used in the following embodiments, unless otherwise indicated, are all purchased from ordinary reagent suppliers.

In all following examples, ACI-35.030 is a liposome formulation according to embodiments of the invention that contains a phosphorylated Tau peptide having the amino acid sequence of SEQ ID NO: 28 at 1200 µg/mL), MPLA (3D-(6-acyl) PHAD®), DMPC, DMPG, cholesterol, a helper T-cell epitope of SEQ ID NO:13 at 300 µg/mL, a CpG oligonucleotide covalently linked to a cholesterol group via a PEG linker, and a buffer, and ACI-35 is a liposome formulation according to embodiments of the invention that contains a phosphorylated Tau peptide having the amino acid sequence of SEQ ID NO: 28, MPLA, DMPC, DMPG, cholesterol, and a buffer.

Example 1: Dose-Response of ACI-35.030 in C57BL/6J Mice

Objective:
To evaluate the immunogenicity of ACI-35.030 vaccine when administered by intramuscular (i.m.) injection to C57BL/6 female mice.

Methods:
The study design is explained in Table 1.

TABLE 1

| Study design of Example 1 | | | | | |
|---|---|---|---|---|---|
| Group | Genotype | Mice | Treatment | Route of administration | Theoretical peptide conc. per mouse dose |
| 1 | C57BL/6 | 10 | ACI-35.030 | Intramuscular | 80 µg |
| 2 | C57BL/6 | 10 | ACI-35.030 | Intramuscular | 35 µg |

Dose administered 3 times at following intervals: Day 1, 15 and 29.
Blood samples for antibody determination withdrawn at following intervals: Day −7, 8, 22 and 36.

Specific IgG antibody responses directed against the phosphorylated Tau peptide (determined by ELISA) were measured.

Results/Conclusions:
Immunization with target dose of 35 and 80 µg of T3 in the ACI-35.030 (1200:300) vaccine induced antibodies directed against the T3.5 peptide having the amino acid sequence of SEQ ID NO:2 (see FIG. 1).

Example 2: Evaluation of IgG Responses Induced by ACI-35.030 (Tetrapalmitoylated T3 phospho-Tau Peptide, MPLA (3D-(6-acyl) PHAD®) and CpG7909-Chol on the Liposome Surface, with Encapsulated T50) Vaccines in Rhesus Macaques Objectives:
To evaluate the immunogenicity of ACI-35.030 (tetrapalmitoylated T3 phospho-Tau peptide, MPLA (3D-(6-acyl) PHAD®) and CpG7909-Chol on the liposome surface, with encapsulated T50) vaccine, administered by subcutaneous or intramuscular injection to male and female rhesus macaques, and to thereby determine the optimal route of administration, and the concentration of the vaccine.

Methods:
The study design is explained in Table 2.

TABLE 2

| Study design of Example 2 | | | |
|---|---|---|---|
| Groups | No. of Animals | Route of administration | Vaccine description Theoretical ratio of peptide (T3:T50) (in µg/mL) |
| 1 | 3♂ + 3♀ rhesus monkeys | s.c. | ACI-35.030 non-concentrated (T3:T50 = 400:400) |
| 2 | 3♂ + 3♀ rhesus monkeys | s.c. | ACI-35.030 concentrated (T3:T50 = 1200:1200) |
| 3 | 3♂ + 3♀ rhesus monkeys | i.m. | ACI-35.030 concentrated (T3:T50 = 1200:1200) |

Theoretical dose for liposomal vaccines was 1800 µg of tetrapalmitoylated phosphopeptide (T3) and 1800 µg of T50 peptide per animal.

Dose was administered 4 times at the following intervals: Day 1, 29, 85 and 169. Blood samples for antibody determination withdrawn at following intervals: Days −14, 8, 22, 36, 50, 64, 78, 92, 106, 120, 134, 148, 162, 176 and 190.

Specific IgG antibody responses directed against the phosphorylated and non-phosphorylated Tau peptides (T3.5 and T3.6, respectively; determined by ELISA), the full-length phospho-Tau (pTau) protein (determined by ELISA)

and the pathological form of Tau extracted from human brain of an Alzheimer's disease patient (human PHF; determined by MSD) were measured. Clinical signs (health, behavioral changes, etc.) were recorded on animals twice daily throughout the study starting on the day of transfer. Body weights were recorded for all animals at least once prior to initiation of treatment and weekly thereafter.

Results/Conclusions:

Overall, neither systemic adverse effects nor persistent skin sensitivity at the injection site could be observed after immunization with any of the vaccine regimens.

Concentrated (1200:1200) and non-concentrated (400:400) ACI-35.030 vaccine induced similar T3.5—and human PHF-specific IgG titers. No difference in T3.5—and human PHF-specific IgG titers was detected between s.c. and i.m. administration of the same vaccine formulation.

Example 3: Repeated Dose Toxicity Study after Eight Subcutaneous Injections of ACI-35 Every Two Weeks in C57BL/6 Mice Followed by a Two-Week Treatment-Free Period (GLP)

Objective:

To evaluate the potential toxicity of ACI-35 following subcutaneous injections every two weeks for 14 weeks in C57BL/6 mice. On completion of the treatment period, designated animals were held for a two week treatment-free period in order to evaluate the reversibility of any findings. In addition, the immunogenicity of ACI-35 was assessed during the study.

Methods:

The study design is explained in Table 3.

TABLE 3

Study design of Example 3

| Group | Number of animals | Route of administration | Dosage-volume (µL/injection) | Dose-level (µg peptide/injection) |
|---|---|---|---|---|
| 1 | 18♂ + 18♀ C57BL/6 Mice | s.c. | 800 | 0 (PBS) |
| 2 | 12♂ + 12♀ C57BL/6 Mice | | 800 | 0 (ACI-35-Empty*) |
| 3 | 12♂ + 12♀ C57BL/6 Mice | | 50 | 24 |
| 4 | 12♂ + 12♀ C57BL/6 Mice | | 200 | 98 |
| 5 | 18♂ + 18♀ C57BL/6 Mice | | 800 | 390 |

*ACI-35-Empty details that the vaccine administered does not contain the active peptide T3.
Dose administered eight times at following intervals: Day 1, 15, 29, 43, 57, 71, 85 and 99.
Blood sample withdrawn at following intervals: Week −2, 4, 6, 8, 19, 12, 14, 16 and 17.
The final 6♂ + 6♀ mice from Groups 1 and 5 were retained for a two week treatment-free period at the end of the study.

Results/Conclusions:

Repeated injection of ACI-35-Empty or ACI-35 at the highest dose-level of 390 µg/injection caused a decrease of Albumin/Globulin (A/G) ratio after eight injections. This change, which is commonly shown in immunized animals, could fit with an increment of the globulin (antibody) plasma fraction and it is explained since all ACI-35 treated animals developed antibodies (in the classes of IgM and IgG). Generally, IgG titers were higher than IgM titers after repeated injections, and females had a tendency to develop more antibodies than the males.

At the sites of injections, local and transient reactions (thickening) were observed in groups treated with ACI-35 at 98 or 390 µg of peptide. At these doses, increased spleen and liver weights and decreased thymus weights in both sexes and increased kidney weights in females only were recorded. At the injection sites, macroscopic findings were seen principally with ACI-35 at 98 and 390 µg/injection. Microscopically, administration of PBS control, ACI-35-Empty or ACI-35 from 24 µg/injection was well tolerated locally. Foamy macrophages and mononuclear inflammatory infiltrates related to empty liposomes were seen at all dose levels with dose-related severity but not in the PBS control group. Sub-acute inflammatory reactions with fibrosis and occasional degeneration/necrosis of the subcutis were slightly increased with ACI-35 at 390 µg/injection.

Administration of ACI-35-Empty or ACI-35 at 390 µg/injection induced extramedullary hematopoiesis in the spleen and liver, and increased myeloid cell numbers in the bone marrow, which were related to administration of empty liposomes. In addition, infiltrates of mononuclear inflammatory cells in multiple systemic organs were seen principally with ACI-35 in females at 390 µg/injection and with a lesser extent with ACI-35 empty. This finding was considered the type of response that could be expected in these animals as it was a strain of mouse that is well known to have a readily inducible immune system and therefore not of clinical importance. The only systemic finding after administration of ACI-35 at 98 µg/injection was extramedullary hematopoiesis in the spleen and liver. There were no systemic findings after administration of ACI-35 at 24 µg/injection.

None of these findings were considered to be adverse according to the study definition in view of their mild to moderate severity, complete or partial recovery after two weeks, and the absence of significant clinical or clinical pathology correlates. Consequently, under the experimental conditions of this study, the ACI-35 dose-level of 390 µg of peptide administered to C57BL/6J male and female mice every two weeks over three months was considered to be the NOAEL (no signs of systemic toxicity, absence of adverse signs at the local level).

Example 4: Six Month Subcutaneous Toxicity Study in the Cynomolgus Monkey Followed by a Four Weeks Recovery Period (GLP) with ACI-35

Objective:

To assess the cumulative toxicity of ACI-35 when administered on seven occasions, subcutaneously to Cynomolgus monkeys, once every four weeks. The reversibility or progression of treatment-related changes or any delayed toxicity was assessed during a four week recovery period for some animals following the treatment period.

Methods:

The study design is explained in Table 4.

TABLE 4

Study design of Example 4

| Group | Number of animals | Route of administration | Dosage-volume (mL/injection) | Dose-level (µg peptide/injection) |
|---|---|---|---|---|
| 1 | 5♂ + 5♀ Cynomolgus monkey | s.c. | 3 | 0 (PBS) |

TABLE 4-continued

Study design of Example 4

| Group | Number of animals | Route of administration | Dosage-volume (mL/injection) | Dose-level (μg peptide/injection) |
|---|---|---|---|---|
| 2 | 3♂ + 3♀ Cynomolgus monkey | | 0.75 | 358 |
| 3 | 3♂ + 3♀ Cynomolgus monkey | | 1.5 | 716 |
| 4 | 5♂ + 5♀ Cynomolgus monkey | | 3 | 1431 |

Dose administered seven times at following intervals: Day 1, 29, 57, 85, 113, 141 and 169.
Blood sample withdrawn at following intervals: Day 15, 43, 71, 99, 127, 155, 183 and 208.
The final 2♂ + 2♀ macaca from Groups 1 and 4 were retained for a four weeks treatment-free period at the end of the study.

Results/Conclusions:

Subcutaneous administration of ACI-35 to Cynomolgus monkeys at 358, 716 and 1431 μg/injection once every 28 days for a period of six months was well-tolerated in all animals.

Although a relationship with treatment could not be excluded, slight increases in neutrophil counts and slight decreases in glucose levels were considered not to be adverse since all the values were within the background historical data and no relevant variations with respect to pretest values were recorded.

All test item-treated groups developed antibodies. Immune response two weeks after the first administration was similar in all test-item-treated groups. Thereafter, mean anti-pTau antibody titers increased throughout the treatment period following a trend for a dose-effect relationship. Animals undergoing the four-week recovery showed a clear decrease with respect to antibody levels recorded two weeks after the seventh administration.

Based on the results obtained and under these study conditions, the dose of 1431 μg/injection administered once every 28 days for six months was considered the NOAEL (No Observed Adverse Effects Level) for this study.

Example 5: Three Months Intramuscular Toxicity Study in Rhesus Monkey Followed by a Four Weeks Recovery Period (GLP) with ACI-35.030

Objective:

The purpose of this study was to assess the potential toxicity of ACI-35.030 when administered in three monthly occurrences, intramuscularly to naïve male and female rhesus monkeys. The reversibility of possible treatment-related changes was assessed on 2 monkeys/sex from control and high dose groups during a four weeks recovery period.

Design:

The study protocol applied was as following (Table 5)

TABLE 5

Study design of Example 5

| Group | Treatment | Number of animals# | Route of administration | Dosage-volume (mL/injection) | Dose-level (μg peptide/injection) |
|---|---|---|---|---|---|
| 1 | ACI-E.030* | 5♂ + 5♀ Rhesus monkey | i.m. | 2 | 0 |
| 2 | ACI-35.030 | 3♂ + 3♀ Rhesus monkey | | 1 | 1200 |
| 3 | ACI-35.030 | 5♂ + 5♀ Rhesus monkey | | 2 | 2400 |

2♂ + 2♀ monkey from Groups 1 and 3 were retained for a four weeks treatment-free period.
*ACI-E.030 a liposome formulation comprising the same components as ACI-35.030, except that it does not contain any Tau peptide The test and reference items were administered by a single intramuscular injection on days 1, 29 and 85 in 3 different sites of the thigh. Throughout the study, all animals were observed at least twice daily for viability/mortality and clinical signs. On each day of administration, animals were subjected to an evaluation for local reactions (Draize scoring) at the dosing site prior to dosing and at 6, 24 and 48 hours post dose.

Food consumption was qualitative estimated for each cage through the study. Body weight was assessed on weekly basis starting from the acclimatization period up the end of the study. Ophthalmoscopy was performed once during pretest and three/four days after the last administration. Electrocardiograms (limb leads I, II and III and augmented leads aVR (Augmented Volt Right), aVL (augmented Volt Left) and aVF (augmented Volt Foot)) was recorded for each animal once during the pretest and approximately 24 hours after the last administration.

Clinical pathology evaluations (hematology, clinical chemistry, coagulation, and urinalysis) was performed on all animals once during the pretest period than 2 days following the last injection (Day 87), and on all surviving animals once towards the end of the recovery period (Day 125).

Blood samples for serum for determination of anti-p-Tau and anti T50 by ELISA were collected on Days −14, 8, 22, 36, 50, 64, 78, 92, 99, 106, 120 and 127 (Day 106, 120 and 127 were for recovery animals only).

PBMCs were harvested at Day −14, two weeks after the last immunization in all groups and prior to necropsy in the recovery group. IL-4 and IFN-γ ELISPOT analyses were performed to determine the tau-specific T-cell response.

Immunophenotyping was assessed in all animals on blood sampled once pretest and at the necropsy.

Blood was collected for PMBCs (ELISpot for T cell response against T3.5) on Days −14 and 99 (Main and Recovery) and Day 127 (Recovery).

Cerebrospinal fluid (CSF) samples were collected under sedation from all animals pretest and prior to each post-mortem examination for cytology evaluation.

Following completion of the scheduled treatment or recovery periods, all animals were necropsied and various organs were weighed. Histopathological examination was performed on the brain, injection sites and lymph nodes of all study animals.

Through immunohistochemical (IHC) techniques, the potential binding activity of the antibodies induced by ACI-35.030 versus different human tissues was evaluated in a dedicated study phase in which the cross-reactivity of ACI-35.030-induced monkey antibodies against human tissues was assessed in a panel of 42 frozen human tissues and blood smears from three unrelated individuals using the serum of animals dosed at 2400 µg T3 sampled on day 99.

Results:

There were neither deaths nor ACI-35.030 related effects on body weights, body changes, appetence, ophthalmology, electrocardiography, clinical pathology (hematology, coagulation, clinical chemistry and urinalysis) or immunophenotyping.

Transient slight to moderate signs of skin irritation (erythema and edema) in the injection sites were observed in a few animals across all groups following immunization. Temporary severe local edema was observed in the treated hindlimb of 1 out of 5 females given 2400 µg T3/injection at 48 hours on Day 29, and on Day 87. However, the edema resolved one day later (Day 30 and Day 88).

Some differences, dose unrelated in mean organ weights were noted between control and test item dosed groups. Macroscopically, the inguinal, iliac and pelvic lymph nodes were randomly described as enlarged across all groups including controls, often correlated microscopically with lymphoid hypercellularity, were mostly recovered following the 4-week recovery period and were interpreted to be likely due to stimulation by the vaccine/vaccine adjuvant. Microscopically, minimal to mild inflammation was observed in the skeletal muscle at the injection site and in the dermis and/or subcutis, accompanied with minimal degeneration and/or regeneration of skeletal muscle were noted across all groups including controls. The inflammation was considered likely due to a combination of injection procedures related to needle puncture and local immune response to the injected material. These changes were not considered to be adverse and were going to be recovered following the 4-week recovery period.

There were no microscopic changes in the brain related to the administration of ACI-35.030.

Figure 2:
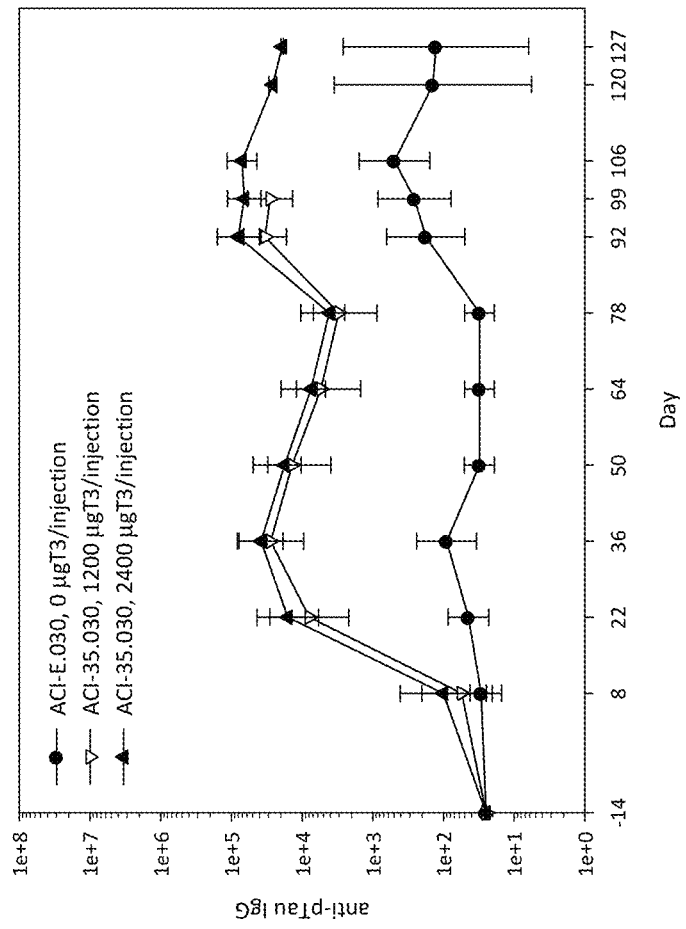
FIG. 2 shows that 1200 µg/dose and 2400 µg/dose of ACI-35.030 induced a sustained titer of anti-phosphorylated tau antibodies in Rhesus macaque; the geometric mean per group of antibody titers expressed in AU/mL, as measured by ELISA, is represented.

ACI-35.030 induced sustained anti-pTau IgG titers at both 1200n/dose and 2400n/dose (FIG. 2).

No tau-specific T-cell response was observed at the end of the treatment, suggesting a low risk of T-cell activation-related toxicity, such as meningoencephalitis.

Figure 3:
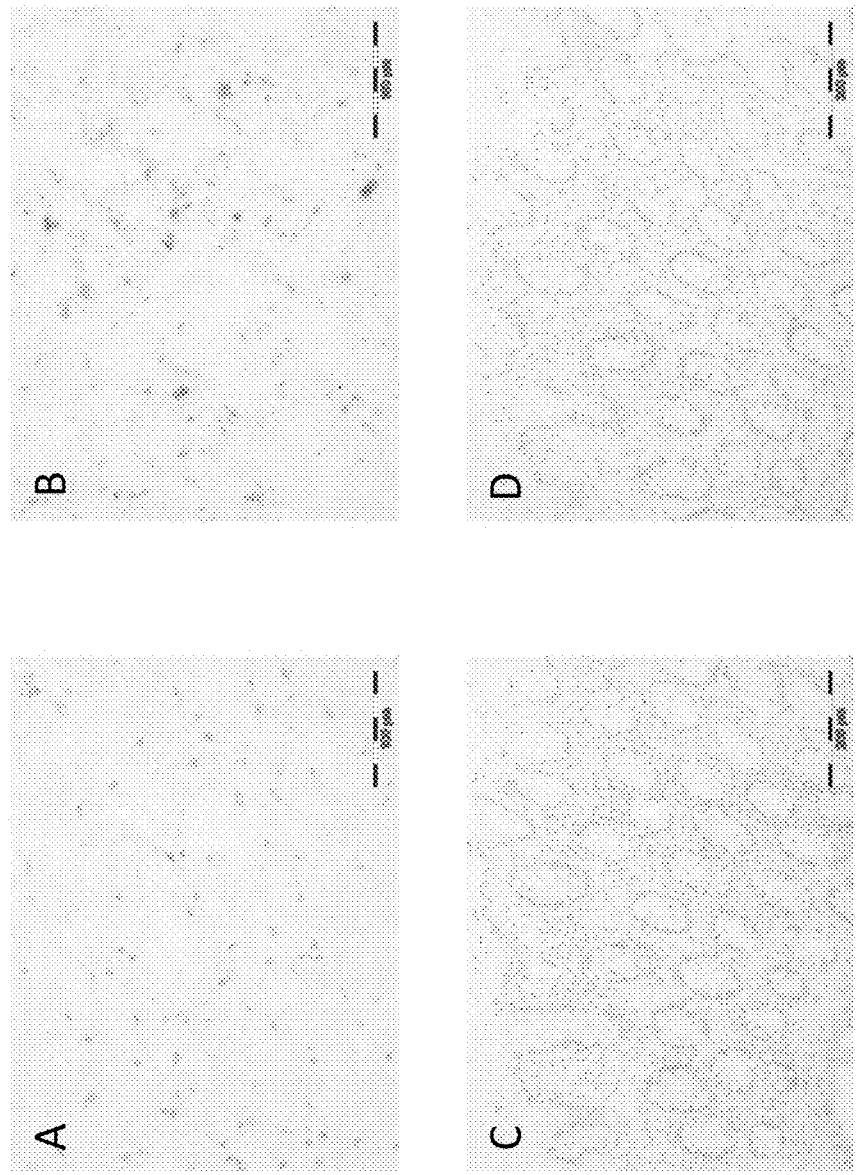
FIG. 3 shows that three injections of 2400 µg/dose of ACI-35.030 induced antibodies that bind to Tau tangles on an AD brain section (Panel B) without cross reactivity with a colon section (Panel D). Pretreatment samples did not bind to the AD brain section (Panel A) or to the colon section (Panel C).

The immunohistochemical investigation conducted on 42 frozen human tissues and blood smears from three unrelated individuals highlighted that the ACI-35.030-induced monkey antibodies, examined at 1/300 and 1/100, specifically stained tau tangles in AD brain sections (FIG. 3, panel A, before treatment with ACI-35.030, panel B: after 3 injections of ACI-35.030 at 2400 µg/dose, serum diluted 1/100,) but did not produce either on- nor off-target staining in any of the tested control tissues. As an example, colon section staining with pre- and post-treatment sera (Panel C and Panel D, respectively) is shown in FIG. 3.

Conclusion:

Overall, due to the absence of ACI-35-related changes after the immunizations on Days 1, 29 and 85, the highest dose level of 2400 µg T3 was considered the no observed effect level (NOEL).

Example 6: EpiScreen™ Immunogenicity Analysis of Peptides

Objective:

Two 16-mer peptides, Tau 393-408[pS396/pS404] (T3.5 having the amino acid sequence of SEQ ID NO:2) and Tau393-408 (T3.6 having the amino acid sequence of SEQ ID NO:4) were tested in EpiScreen™ time course T-cell assays for the capacity to induce CD4$^+$ T-cell response in 51 human donors.

Design:

EpiScreen™ Time Course T-Cell Proliferation Assays and IL-2 ELISPOT Assays

PBMCs from 51 human donors were stimulated with either peptide at a final concentration of 5 µM. For each donor, a reproducibility control (cells incubated with 100 µg/mL KLH), a benchmark clinical control (cells incubated with 0.3 µM humanized A33) and a culture medium only well were also included. Proliferation and IL-2 production were evaluated after different time points.

EpiScreen™ data Analysis

For proliferation assays and IL-2 ELISPOT assays, an empirical threshold of a Stimulation Index (SI) equal to or greater than two (SI≥2.00) has been previously established whereby samples inducing responses above this threshold are deemed positive whereas SI≥1.90 were considered as borderline responders.

Previous EpiScreen™ time course T-cell assays with a range of biologics have shown a clear correlation between the percentage of donor T-cell responses in the EpiScreen™ assay and the level of immunogenicity observed in the clinic. In general, protein therapeutics that induce >10% positive responses in the EpiScreen™ assay are associated with a significant risk of immunogenicity in the clinic.

Results:

The overall correlation between proliferation and IL-2 ELISPOT assays was high (98% for KLH) and thus responding donors were defined as those that mounted a positive response to each sample in both IL-2 ELISPOT and proliferation assays. Analysis of the combined datasets from these two assays revealed that one out of 51 (2%) donors responded to Tau 393-408 [pS396/pS404] and two out of 51 (4%) donors responded to Tau 393-408. When taking into account borderline responses and donors responding in only one of the two assays, four out of 51 donors (8%) responded to Tau 393-408 [pS396/pS404] and four out of 51 donors (8%) responded to Tau 393-408. Thus, the overall frequency and magnitude of responses was low for both peptides with a maximum of 8% of donors responding.

Conclusion:

The ability of the test peptides (Tau 393-408 [pS396/pS404] and Tau 393-408) to induce CD4$^+$ T-cell responses measured by proliferation and IL-2 secretion was tested against a cohort of 51 HLA-typed donors. Data from the study indicated that the overall relative risk of inducing CD4$^+$ T-cell responses was low (2-8%) for both peptides.

In comparison with protein therapeutics tested in EpiScreen™ assays, the data from this study shows that both peptides would be considered as having a low potential risk of inducing CD4$^+$ T-cell responses in human.

Example 7: Safety and Efficacy of ACI-35 in Humans

The safety, tolerability and immunogenicity of ACI-35 vaccine (ACI-35) was evaluated in a clinical phase Ib study conducted in patients with mild to moderate AD in UK and Finland (ACI-35-1201: A Phase Ib Multicenter, Double-Blind, Randomized, Placebo-Controlled Study of the Safety, Tolerability and Immunogenicity of ACI-35 in Patients with Mild to Moderate Alzheimer's Disease).

Objective:

To assess preliminarily ACI-35 at 3 doses and 3 dosing regimens in patients with mild to moderate AD for the safety and tolerability, and for the induction of anti-phospho-Tau (pTau) immunoglobulin G (IgG) titer in serum.

Methods:

Each of the 5 cohorts consisted of a different dose (300 µg, 900 µg or 1800 µg of tetrapalmitoylated phosphopeptide (pTau Peptide T3, SEQ ID NO: 28)) and/or dosing regimen spread over 6 months (2, 3 or 5 dose administrations), followed by a booster injection 12-16 months (cohort 1) or 6 months (cohorts 2-5) after the last injection, as described in Table 5.

TABLE 5

Study design of Example 5

| Cohort | N | Dose µg | W0 | W4 | W8 | W12 | W24 | +W48 (dose µg) | +W48-W76 (dose µg) |
|---|---|---|---|---|---|---|---|---|---|
| 1 | 4 | 300 | X | X | X | X | X |  | X (900) |
| 2 | 8 | 900 | X | X | X | X | X | X (900) |  |
| 3 | 4 | 900 | X | X |  |  | X | X (900) |  |
| 4 | 4 | 1800 | X | X |  |  | X | X (1800) |  |
| 5 | 4 | 1800 | X |  |  |  | X | X (1800) |  |

Abbreviations:
N = Number of patients,
w = Week

Twenty-four patients were randomized and received at least 1 dose of study drug vaccine. The mean patient age was 73.6±5.88 years and the mean MMSE score was 23.3±2.71 at screening. Fifteen females and 9 males were randomized. Twenty-two patients completed the study. Two patients from cohort 2 (one on 900 µg, one on placebo) discontinued the study due to a significant medical condition unrelated to ACI-35 which seriously hampered or made the completion of the study impossible.

Inclusion criteria were as follows:
1. Probable Alzheimer's Disease (AD) according to National Institute of Neurological and Communicative Diseases and Stroke-Alzheimer's Disease and Related Disorders Association criteria
2. Age equal to or over 60 and equal to or less than 85 years
3. Mini Mental State Examination (MMSE) 18-28 points at screening
4. Patient had to be receiving a stable dose of acetylcholinesterase inhibitors for at least 3 months prior to screening
5. Patient cared for by a reliable spouse or other live-in caregiver who gave written consent to assist with clinical assessments and report safety issues
6. Patient who in the opinion of the investigator were able to understand and sign written informed consent, and to comply with all study procedures (Note that consent had to be obtained prior to conducting any trial-related procedures)
7. Women had to be postmenopausal for at least 1 year and/or surgically sterilized
8. Female partner of male patients who were not postmenopausal or surgically sterilized had to use reliable contraceptive measures e.g. double barrier contraception or hormonal contraception Results/Conclusions:

Overall, ACI-35 was safe and well tolerated at all doses and treatment regimens tested in human subjects, while the injection led to a rapid induction of anti-pTau antibodies shortly after the first injection in all study cohorts. Injection site erythema, injection site reactions, and fatigue were the most common study drug-related Treatment Emergent Adverse Events (TEAE). There was no evidence clinically or from laboratory or radiology findings to suggest the development of CNS inflammation. Except for injection site reactions, no pattern of AEs compared to placebo suggested a relationship to study medication. The injection site reactions which were generally mild and self-limiting, were more frequent at higher doses and were reported by all patients on active medication in cohorts 4 and 5. Asymptomatic hypoglycemia was observed more commonly on active medication than on placebo but is of uncertain relationship to the study medication given the known spontaneous occurrence of this phenomenon. Five SAEs were reported, all in patients from cohort 2, of which 1 patient was treated with placebo and experienced 2 SAEs (urosepsis and pyelonephritis). These 2 SAEs were not study drug-related. Three possibly study drug-related SAEs (acute pyelonephritis, sinus node dysfunction and dizziness) were reported for 2 patients treated with ACI-35 being the only observed adverse reaction. No deaths were reported in this study.

Example 7: Safety and Efficacy of ACI-35.030 in Humans

The safety, tolerability and immunogenicity of ACI-35.030 vaccine (ACI-35.030) is evaluated in a clinical Phase Ib/IIa multicenter, double blind, randomized, placebo-controlled study conducted in patients with early AD (mild cognitive impairment (MCI) due to AD and mild AD) in Europe (ACI-35-1802 study).

Objective:

To assess preliminarily ACI-35.030 at up to 3 doses in participants with early AD (e.g., mild cognitive impairment (MCI) due to AD and mild AD), for the safety and tolerability in participants with early AD, and for the induction of immune response against the abnormal form of Tau protein, including induction of anti-phospho-Tau (anti-pTau) in serum, in a time frame of 74 weeks.

Secondary Objectives:

To further assess the immunogenicity of study vaccines by assessing, e.g., the induction of IgG titers against Tau and of IgM titers against pTau and Tau in serum; and to assess the avidity of antibodies elicited by immunization, in a time frame of 74 weeks.

Exploratory Objectives:

To explore the effect of study vaccines on putative biomarkers of the progression of AD, i.e. blood and/or CSF concentrations of total Tau and pTau proteins; to explore the effect of study vaccines on the activation of T-cell in blood; to explore the effect of study vaccines on blood inflammatory cytokines (e.g. IL-1β, IL-2, IL-6, IL-8, IL-10, IFN-γ, and TNF-α); to explore the effect of study vaccines on behavior, cognitive and functional performance, each in a time frame of 74 weeks.

Methods:

Each of 3 cohorts consists of patients receiving different dose of ACI-35.030, referred to by the amount of pTau Peptide T3 in the composition (300 µg, 900 µg or 1800 µg of tetrapalmitoylated phosphopeptide pTau Peptide T3, SEQ ID NO: 28) spread over 48 weeks (dose administrations at weeks 0, 8, 24 and 48), followed by a 24-week (6 months) safety follow-up period.

Twenty-four patients are randomized into the 3 sub-cohorts, with 2 patients receiving placebo and 6 patients receiving ACI-35.030 in each sub-cohort. Dosages are administered intramuscularly.

A safety assessment is performed immediately after each dosing and 48 to 72 hours thereafter by telephone call for all study patients. In each sub-cohort, the first dosing of the first 4 patients is performed once the safety assessment at 48 to 72 hours of the previous patient has been performed to confirm there is no clinically relevant safety issue related to study vaccine, according to the site principal investigator.

All treated patients have a safety follow-up period of 24 weeks (6 months) after the end of the treatment period. During this period, patients are asked to attend a first follow-up visit 19 weeks after the last administration and a last visit at the end of the follow-up period (26 weeks after the last administration). Participants' safety is monitored throughout the study with regular review of safety data by a Data and Safety Monitoring Board (DSMB).

Interim analyses will be carried out as follows:

The first interim analysis is conducted once all cohort 1 patients have completed visit 4 (Week 10), i.e. 2 to 4 weeks after the second injection. The objective is to review safety, tolerability, and immunogenicity data up to this time point in order to determine whether to start cohort 2.

The second interim analysis is conducted once all cohort 2 patients have completed visit 4 (Week 10), i.e. 2 to 4 weeks after the second injection. The objective is to collect safety, tolerability and immunogenicity data up to this time point in order to determine whether to start cohort 3.

The third interim analysis is conducted once all cohort 3 patients have completed visit 6 (Week 26), i.e. 2 to 4 weeks after the third injection. The objective is to decide to expand either cohort 1, 2 or 3 in order to collect additional safety/tolerability data at the dose presenting the most favorable profile in terms of immunogenicity, safety and tolerability.

The fourth interim analysis is performed at the end of the treatment period (i.e. 2 to 4 weeks after the 4th injection). The objective is to review the safety/tolerability and immunogenicity data up to this time point, including data from patients of sub-cohort expansion if applicable. Biomarker results can be included as supportive exploratory data. The results are compared with those subsequently obtained for other cohorts in order to select, among all study cohorts, the best strategy for further clinical development.

The fifth interim analysis is performed at the end of the safety follow-up period, i.e. once all cohort 1 patients have completed visit 11 (Week 74). The objective is the same as in the fourth interim analysis and the results are subsequently compared across all cohorts.

The study population is 50-75 years of age (male and female) with a diagnosis of mild AD or MCI due to AD according to NIA-AA criteria.

Inclusion criteria are as follows:
1. Male or female with age from 50 and up to 75 years old inclusive.
2. Mild Cognitive Impairment (MCI) due to AD or mild AD according to NIA-AA criteria and a Clinical Dementia Rating scale (CDR) global score of 0.5 or 1.
3. Mini mental state examination (MMSE) score of 22 or above.
4. Levels of CSF amyloid beta 42 (Aβ42) and phosphorylated Tau at screening consistent with NIA-AA 2018 criteria for AD pathology. In borderline cases for CSF Aβ42 levels, other results may be considered to help determine amyloid positivity e.g. the Aβ42/Aβ40 ratio and, on a case by case basis, a history of positive amyloid PET scan or positive CSF Aβ42 level. Results from CSF sampling performed within 3 months prior to screening are acceptable on a case by case basis provided that they are consistent with the presence of amyloid pathology and that the corresponding CSF sample can be used in the study for testing.
5. Patients either not taking any marketed treatment for AD or receiving a stable dose of an acetylcholinesterase inhibitor and/or memantine for at least 3 months prior to baseline.
6. Patients cared for by a reliable informant or caregiver to assure compliance, assist with clinical assessments and report safety issues.
7. Women must be post-menopausal for at least one year and/or surgically sterilized. Women of childbearing potential or not post-menopausal must have a negative pregnancy test at screening and be willing to use highly effective methods of contraception from the screening visit until the end of their participation. Urine pregnancy re-test will be performed throughout the treatment period to determine if the subject can continue receiving the study vaccine. Male patients with partners of child bearing potential must be willing to use appropriate contraceptive measures during the study.
8. Patient who in the opinion of the investigator is able to understand and provide written informed consent.
9. Patients and informant or caregiver must be fluent in one of the languages of the study and able to comply with all study procedures, including lumbar punctures.

Exclusion criteria are as follows:
1. Participation in previous clinical trials for AD and/or for neurological disorders using active immunization unless there is documented evidence that the patient was treated with placebo only and the placebo formulation is not expected to induce any specific immune response.
2. Participation in previous clinical trials for AD and/or for neurological disorders using any passive immunization within the past 12 months prior to screening unless there is documented evidence that the subject was treated with placebo only and the placebo is not expected to induce any specific immune response.
3. Participation in previous clinical trials for AD and/or for neurological disorders using any small molecule drug including BACE-1 inhibitors within the past 3 months prior to screening.
4. Concomitant participation to any other clinical trial using experimental or approved medications or therapies.
5. Presence of positive anti-nuclear antibody (ANA) titers at a dilution of at least 1/160 in patients without clinical symptoms of auto-immune disease.
6. Current or past history of auto-immune disease, or clinical symptoms consistent with the presence of auto-immune disease.
7. Immune suppression including but not limited to the use of immunosuppressant drugs or systemic steroids unless they have been prescribed transiently more than 3 months prior to screening.
8. History of severe allergic reaction (e.g., anaphylaxis) including but not limited to severe allergic reaction to previous vaccines and/or medications.
9. Prior history of clinically significant hypoglycemic episodes.
10. Drug or alcohol abuse or dependence currently met or within the past five years according to Diagnostic and Statistical Manual of Mental Disorders-V (DSM-V) criteria.
11. Any clinically significant medical condition likely to interfere with the evaluation of safety and tolerability of the study treatment and/or the adherence to the full study visit schedule.

12. Any clinically significant medical condition likely to impact on the immune system and/or expected to potentially impair the immunization potential of the study vaccine in patients (e.g., any history of acquired or innate immunodepressive disorder).
13. Use of hydralazine, procainamide, quinidine, isoniazide, TNF-inhibitors, minocycline within the last 12 months prior to screening.
14. Use of diltiazem unless on a stable dose for at least 3 months prior to screening.
15. Significant risk of suicide defined, using the Columbia-Suicide Severity Rating Scale, as the subject answering: "yes" to suicidal ideation questions 4 or 5 or answering: "yes" to suicidal behavior within the past 12 months.
16. Concomitant psychiatric or neurologic disorder other than those considered to be related to AD (e.g. head injury with loss of consciousness, symptomatic stroke, Parkinson's disease, severe carotid occlusive disease, TIAs).
17. History or presence of uncontrolled seizures. If history of seizures, they must be well controlled with no occurrence of seizures within 2 years prior to baseline. The use of anti-epileptic medications is permitted if at stable dose for at least 3 months prior to screening.
18. History of meningoencephalitis within the past 10 years prior to screening.
19. Patients with a history of hemorrhagic and/or non-hemorrhagic stroke.
20. Presence or history of peripheral neuropathy.
21. History of inflammatory neurological disorders with potential for CNS involvement.
22. Screening MRI scan showing structural evidence of alternative pathology not consistent with AD which could cause the patient's symptoms. Evidence of space occupying lesions other than benign meningioma of less than 1 cm diameter, more than two lacunar infarcts or one single infarct larger than 1 cm in diameter or any single area of superficial siderosis or evidence of a prior macro-hemorrhage ≥10 mm. Microbleeds on T2*MRI are allowed up to a maximum of 10, regardless of the location.
23. MRI examination cannot be done for any reason, including but not limited to metal implants contraindicated for MRI studies and/or severe claustrophobia.
24. Significant hearing or visual impairment or other issues judged relevant by the investigator preventing to comply with the protocol and to perform the outcome measures.
25. Clinically significant infections or major surgical operation within 3 months prior to screening. Planned surgery anticipated to occur during participation in the study must be reviewed and approved by the medical monitor at screening.
26. Any vaccine received within the past 2 months before baseline, including influenza vaccine.
27. Clinically significant arrhythmias or other clinically significant abnormalities on ECG at screening.
28. Myocardial infarction within one year prior to baseline, unstable angina pectoris, or significant coronary artery disease.
29. Patients with a history of cancer within the past 5 years other than treated squamous cell carcinoma, basal cell carcinoma and melanoma in situ, or in-situ prostate cancer or in-situ breast cancer which have been fully removed and are considered cured.
30. In the opinion of the site investigator, clinically significant deviations from normal values for hematologic parameters, liver function tests, and other biochemical measures, that are judged to be clinically significant.
31. Female subjects being pregnant as confirmed by serum testing at screening or planning to be pregnant or lactating.
32. Patient receiving any anticoagulant drug or antiplatelet drug, except aspirin at doses lower than 100 mg daily (in order to avoid risk of bleeding during scheduled or unscheduled lumbar puncture).
33. Patients receiving antipsychotic drugs unless on stable low doses for the treatment of insomnia.
34. Patients who have donated blood or blood products during the 30 days prior to screening or who plan to donate blood while participating in the study.
35. Positive VDRL (Venereal Disease Research Laboratory) consistent with active syphilis at screening.
36. Patients with a positive HIV test at screening.
37. Patients with active hepatitis B and/or C as measured by testing at screening.
38. Patients with creatinine greater than 1.5× upper limit of normal, abnormal thyroid function tests or clinically significant reduction in serum B12 or folate levels (note: all oral doses of thyroid replacement agents, B12 or folate have to be stable for at least 3 months prior to screening).

Results/Conclusions:

The following primary endpoints will be assessed:

Safety and tolerability—adverse events, immediate and delayed reactogenicity (e.g. anaphylaxis, local and systemic reactogenicity, including pain, redness, immune-complex disease, swelling, fever); global assessment of tolerability; suicidal ideation (C-SSRS); behavior (NPI); cognitive and functional assessments (RBANS, CDR-SB) to assess safety; vital signs; MRI imaging; electrocardiogram; routine hematology and biochemistry evaluation in blood and urine; evaluation of autoimmune antibodies including anti-DNA antibodies in blood; inflammatory markers in blood and CSF.

Immune response—anti-pTau IgG titers in serum (geometric mean, change from baseline, responder rate, peak and area under the curve).

The following secondary endpoints will be assessed:

Immune response—anti-Tau IgG, anti-pTau and anti-Tau IgM titers in serum (geometric mean, change from baseline, responder rate, peak and area under the curve), determination of IgG response profile by avidity testing.

The following exploratory endpoints will be assessed:

Change from baseline of biomarkers titers in blood and/or CSF (e.g. total Tau and pTau proteins), change from baseline in T-cell activation level in blood, change from baseline of inflammatory cytokine (e.g. IL-1B, IL-2, IL-6, IL-8, IL-10, IFN-γ, and TNF-α) titers in blood, change from baseline in suicidal ideation (C-SSRS), behavior (NPI), cognitive and functional performance (RBANS, CDR-SB) scores.

Example 8: Intramuscular Injection Induced a More Homogeneous Immune Response than a Subcutaneous Injection Groups of Rhesus macaques (n=3 males and 3 females per group) were immunized intramuscularly or subcutaneously by vaccination at day 1, day 29, day 85 and day 169 with 1800 µg/dose of ACI-35.030.

Figure 4:
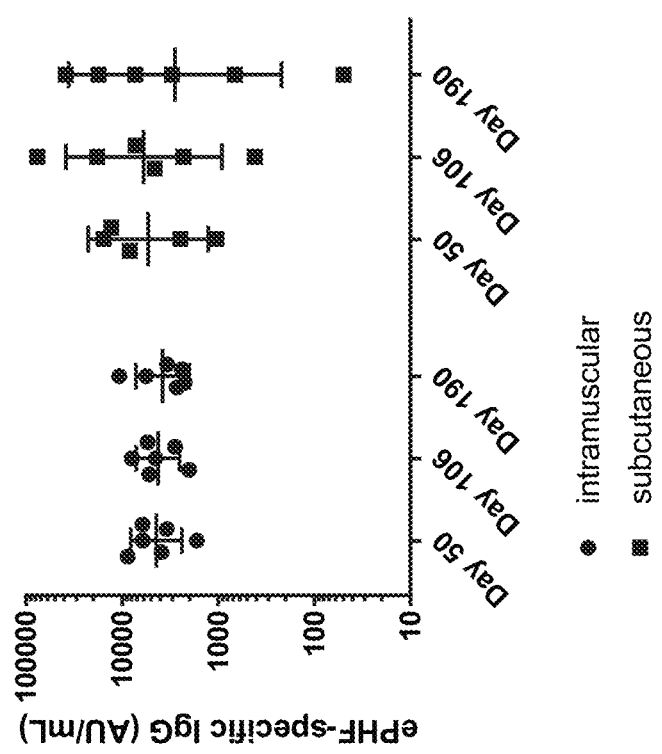
FIG. 4 shows that intramuscular injection of 1800 µg/dose of ACI-35.030 induced anti-ePHF IgG antibody titers with a lower intragroup variability as compared to the subcutaneous injection of the same vaccine at the same dose.

Preparations of enriched paired helical filaments (ePHF) were obtained from post-mortem brain tissues of histologically confirmed AD subjects by sarcosyl extraction of insoluble tau, using a modified method of Greenberg and Davies (1991, *Proc Natl Acad Sci USA*, 87(15):5827-31). Antibody titers specific for enriched paired helical filaments (ePHF) were evaluated using the Mesoscale Discovery (MSD) platform. MSD streptavidin plates were coated with the biotinylated anti-tau capturing antibody (HT7-biotin, ThermoScientific) before incubation with ePHF isolated from AD patients, while the IgG antibodies specific for ePHF were further detected using a SulfoTag-labelled anti-human IgG antibody that cross-reacts with monkey IgG antibodies. More specifically, ePHF was added to MSD Gold small spot streptavidin 96-well plates (MSD) previously saturated with 1% BSA and coated with biotinylated HT-7 (Thermo Scientific). After one hour of incubation, plates were washed with PBST and serial dilutions of sera were added and incubated for two hours. Bound antibodies were detected using a SulfoTag labelled anti-human IgG antibody followed by a fixation step in 1% PFA before adding the Read Buffer T. Plates were analyzed using a Sector Imager (MSD). Results were expressed in Arbitrary units per milliliter (AU/mL) for each individual monkey, together with the geometric mean per group (FIG. 4). Antibody titers specific for ePHF at Day 50, Day 106 and Day 190 after the first immunization are represented.

FIG. 4 shows that the liposomal vaccine induced high ePHF-specific IgG titers and that intramuscular injections induced more homogenous antibody responses than subcutaneous injections.

```
SEQUENCE LISTING
SEQ ID NO: 1 - phospho-Tau peptide (7.1)
GDRSGYS[pS]PG[pS]PG[pT]PGSRSRT SEQ ID NO: 2 - phospho-Tau peptide (T3.5)
VYK[pS]PVVSGDT[pS]PRHL SEQ ID NO: 3 - phospho-Tau peptide (22.1)
SSTGSIDMVD[pS]PQLA[pT]LA SEQ ID NO: 4 - Tau peptide (T3.6)
VYKSPVVSGDTSPRHL SEQ ID NO: 5 - phospho-Tau peptide
RENAKAKTDHGAEIVYK[pS]PVVSGDT[pS]PRHL SEQ ID NO: 6 - phospho-Tau peptide
RQEFEVMEDHAGT[pY]GL SEQ ID NO: 7 - phospho-Tau peptide
PGSRSR[pT]P[pS]LPTPPTR SEQ ID NO: 8 - phospho-Tau peptide
GYSSPG[pS]PG[pT]PGSRSR SEQ ID NO: 9 - phospho-Tau peptide
GDT[pS]PRHL[pS]NVSSTGSID SEQ ID NO: 10 - phospho-Tau peptide
PG[pS]PG[pT]PGSRSR[pT]P[pS]LP SEQ ID NO: 11 - phospho-Tau peptide
HL[pS]NVSSTGSID SEQ ID NO: 12 - phospho-Tau peptide
VSGDT[pS]PRHL SEQ ID NO: 13 - T50 T cell epitope
AKFVAAWTLKAAAVVRQYIKANSKFIGITELVVRFNNFTVSFWLRVPKV

SASHLE-NH2
```

```
SEQ ID NO: 14 - T46 T cell epitope
AKFVAAWTLKAAAGSQYIKANSKFIGITELGSFNNFTVSFWLRVPKVSA SHLEK(Pal)K(Pal)-NH2

SEQ ID NO: 15 - T48 helper T cell epitope
AKFVAAWTLKAAAGSQYIKANSKFIGITELGSFNNFTVSFWLRVPKVSA

SHLEGSLINSTKIYSYFPSVISKVNQ-NH2

SEQ ID NO: 16 - T51 helper T cell epitope
AKFVAAWTLKAAARRQYIKANSKFIGITELRRFNNFTVSFWLRVPKVSA

SHLE-NH2

SEQ ID NO: 17 - T52 helper T cell epitope
AKFVAAWTLKAAARKQYIKANSKFIGITELRKFNNFTVSFWLRVPKVSA

SHLE-NH2

SEQ ID NO: 18 - CpG 2006 (also known as CpG 7909)
5'-tcgtcgttttgtcgttttgtcgtt-3'
wherein lower case means phosphorothioate (ps)
internucleotide linkages SEQ ID NO: 19 - CpG 1018
5'-tgactgtgaacgttcgagatga-3'
wherein lower case means phosphorothioate internucleotide linkages SEQ ID NO: 20 - CpG2395
5'-tcgtcgttttcggcgcgcgccg-3'
wherein lower case means phosphorothioate internucleotide linkages SEQ ID NO: 21 - CpG2216
5'-ggGGGACGATCGTCgggggg-3'
wherein lower case means phosphorothioate internucleotide linkages and capital letters means
phosphodiester (po) linkages SEQ ID NO: 22 - CpG2336
5'-gggGACGACGTCGTGgggggg-3',
wherein lower case means phosphorothioate internucleotide linkages and capital letters means
phosphodiester linkages SEQ ID NO: 23 - Pan DR epitope (PADRE) peptide
AKFVAAWTLKAAA

SEQ ID NO: 24 - P2
QYIKANSKFIGITEL

SEQ ID NO: 25 - P30
FNNFTVSFWLRVPKVSASHLE

SEQ ID NO: 26 - TT586-605
LINSTKIYSYFPSVISKVNQ

SEQ ID NO: 27 - palmitoylated phospho-Tau peptide
(palmitoylated 7.1)
K(pal)K(pal)GDRSGYS[pS]PG[pS]PG[pT]PGSRSRTK(pal)

K(pal)

SEQ ID NO: 28 - palmitoylated phospho-Tau peptide
(T3, palmitoylated T3.5)
K(pal)K(pal)VYK[pS]PVVSGDT[pS]PRHLK(pal)K(pal)

SEQ ID NO: 29 - palmitoylated phospho-Tau peptide
(palmitoylated 22.1)
K(pal)K(pal)SSTGSIDMVD[pS]PQLA[pT]LAK(pal)K(pal)

SEQ ID NO: 30 - palmitoylated Tau peptide
K(pal)K(pal)VYKSPVVSGDTSPRHLK(pal)K(pal)

SEQ ID NO: 31 - palmitoylated phospho-Tau peptide
K(pal)K(pal)RENAKAKTDHGAEIVYK[pS]PVVSGDT[pS]PRHLK (pal)K(pal)
```

SEQ ID NO: 32 - palmitoylated phospho-Tau peptide
K(pal)K(pal)RQEFEVMEDHAGT[pY]GLK(pal)K(pal)

SEQ ID NO: 33 - palmitoylated phospho-Tau peptide
K(pal)K(pal)PGSRSR[pT]P[pS]LPTPPTRK(pal)K(pal)

SEQ ID NO: 34 - palmitoylated phospho-Tau peptide
K(pal)K(pal)GYSSPG[pS]PG[pT]PGSRSRK(pal)K(pal)

SEQ ID NO: 35 - palmitoylated phospho-Tau peptide
K(pal)K(pal)GDT[pS]PRHL[pS]NVSSTGSIDK(pal)K(pal)

SEQ ID NO: 36 - palmitoylated phospho-Tau peptide
K(pal)K(pal)PG[pS]PG[pT]PGSRSR[pT]P[pS]LPK(pal)K(pal)

SEQ ID NO: 37 - palmitoylated phospho-Tau peptide
K(pal)K(pal)HL[pS]NVSSTGSIDK(pal)K(pal)

SEQ ID NO: 38 - palmitoylated phospho-Tau peptide
K(pal)K(pal)VSGDT[pS]PRHLK(pal)K(pal)

SEQ ID NO: 39 - T50 without the C-terminal amide
AKFVAAWTLKAAAVVRQYIKANSKFIGITELVVRFNNFTVSFWLRVPKVSASHLE SEQ ID NO: 40 - T46 without the -Lys(Pal)-Lys(Pal)-NH$_2$ at the C-terminal
AKFVAAWTLKAAAGSQYIKANSKFIGITELGSFNNFTVSFWLRVPKVSASHLE SEQ ID NO: 41 - T48 without the C-terminal amide
AKFVAAWTLKAAAGSQYIKANSKFIGITELGSFNNFTVSFWLRVPKVSASHLEGSLINSTKIYSYFPSVISKVNQ SEQ ID NO: 42 - T51 without the C-terminal amide
AKFVAAWTLKAAARRQYIKANSKFIGITELRRFNNFTVSFWLRVPKVSASHLE SEQ ID NO: 43 - T52 without the C-terminal amide
AKFVAAWTLKAAARKQYIKANSKFIGITELRKFNNFTVSFWLRVPKVSASHLE SEQ ID NO: 44 - T57
AKFVAAWTLKAAAVVRQYIKANSKFIGITELVVRFNNFTVSFWLRVPKVSASHLE-K(Pal)K(Pal)-NH2

---

It is claimed:

1. A method of inducing anti-phosphorylated Tau antibodies without inducing a severe adverse event in a human subject in need thereof, comprising administering to the subject an effective amount of liposomes comprising a toll-like receptor 4 agonist and a Tau phosphopeptide comprising an amino acid sequence selected from the group consisting of SEQ ID NO:1 to SEQ ID NO:3 and SEQ ID NO:5 to SEQ ID NO:12, wherein the Tau phosphopeptide is administered to the human subject at an amount of about 25 nmoles to about 750 nmoles per dose, and the Tau phosphopeptide is presented on the surface of the liposome.

2. The method of claim 1, wherein the Tau phosphopeptide consists of an amino acid sequence selected from the group consisting of SEQ ID NO:27 to SEQ ID NO:29 and SEQ ID NO:31 to SEQ ID NO:38.

3. The method of claim 1, wherein the effective amount of liposomes comprises 100 μg to 2500 μg per dose of the Tau phosphopeptide.

4. The method of claim 3, wherein the effective amount of liposomes comprises 300μg per dose, 900 μg per dose, 1800 μg per dose, or 2400 μg per dose of the Tau phosphopeptide.

5. The method of claim 1, wherein the liposomes are administered subcutaneously.

6. The method of claim 1, wherein the liposomes are administered intramuscularly.

7. The method of claim 1, further comprising administering to the subject a second dose of the effective amount of liposomes 1 to 24 weeks after the initial administration.

8. The method of claim 1, wherein the liposome further comprises a helper T-cell epitope and a lipidated CpG oligonucleotide.

9. The method of claim 8, wherein the lipidated CpG oligonucleotide has a nucleotide sequence selected from the group consisting of SEQ ID NO:18 to SEQ ID NO:22, wherein the CpG oligonucleotide has one or more phosphorothioate internucleotide linkages, and the CpG oligonucleotide is covalently linked to at least one lipophilic group, optionally via a PEG linker.

10. The method of claim 9, wherein the CpG oligonucleotide is covalently linked to at least one lipophilic group via a PEG linker.

11. The method of claim 1, wherein the liposome further comprises one or more lipids selected from the group consisting of 1,2-dimyristoyl-sn-glycero-3-phosphocholine (DMPC), 1,2-dimyristoyl-sn-glycero-3-phosphoryl-3'-rac-glycerol (DMPG), and cholesterol.

12. The method of claim 8, wherein the helper T-cell epitope comprises at least one amino acid sequence selected from the group consisting of SEQ ID NO:13 to SEQ ID NO:17, SEQ ID NO:23 to SEQ ID NO:26, and SEQ ID NO:39 to SEQ ID NO:44.

13. The method of claim 8, wherein the effective amount of liposomes comprises the helper T-cell epitope at an amount of about 2 nmoles to about 110 nmoles per dose.

14. The method of claim 8, wherein the effective amount of liposomes comprises the helper T-cell epitope having an amino acid sequence selected from the group consisting of SEQ ID NO:13 to SEQ ID NO:17, SEQ ID NO:23 to SEQ ID NO:26, and SEQ ID NO:39 to SEQ ID NO:44 at an amount of 25 μg to 620 μg per dose.

15. The method of claim 1, wherein the effective amount of liposomes comprises the toll-like receptor 4 agonist at an amount of 30 μg to 900 μg per dose.

16. The method of claim 8, wherein the effective amount of liposomes comprises the lipidated CpG oligonucleotide having a nucleotide sequence selected from the group consisting of SEQ ID NO:18 to SEQ ID NO:22 at an amount of 50 μg to 1250 μg per dose.

17. The method of claim 1, wherein the liposome comprises:
    (1) the Tau phosphopeptide having the amino acid sequence of SEQ ID NO:28;
    (2) the toll-like receptor 4 agonist comprising monophosphoryl hexa-acyl Lipid A, 3-deacyl;
    (3) the helper T-cell epitope comprising the amino acid sequence of SEQ ID NO: 39;
    (4) the lipidated CpG oligonucleotide comprising the nucleotide sequence of SEQ ID NO:18; and
    (5) at least one lipid selected from the group consisting of 1,2-dimyristoyl-sn-glycero-3-phosphocholine (DMPC), 1,2-dimyristoyl-sn-glycero-3-phosphoryl-3'-rac-glycerol (DMPG), and cholesterol.

18. The method of claim 1, wherein the subject is in need of a treatment of Alzheimer's Disease.

19. A method of inducing anti-phosphorylated Tau antibodies without inducing a severe adverse event in a human subject in need thereof, comprising administering to the subject an effective amount of liposomes comprising:
    (1) a Tau phosphopeptide having the amino acid sequence of SEQ ID NO:28;
    (2) a toll-like receptor 4 agonist comprising monophosphoryl hexa-acyl Lipid A, 3-deacyl;
    (3) a helper T-cell epitope comprising the amino acid sequence of SEQ ID NO: 39;
    (4) a lipidated CpG oligonucleotide comprising the nucleotide sequence of SEQ ID NO:18; and
    (5) at least one lipid selected from the group consisting of 1,2-dimyristoyl-sn-glycero-3-phosphocholine (DMPC), 1,2-dimyristoyl-sn-glycero-3-phosphoryl-3'-rac-glycerol (DMPG), and cholesterol,
    wherein the effective amount of liposomes comprises 300 μg to 2400 μg per dose of the Tau phosphopeptide, 100 μg to 585 μg per dose of the toll-like receptor 4 agonist, 75 μg to 450 μg per dose of the helper T-cell epitope, and 150 μg to 800 μg per dose-lipidated CpG oligonucleotide.

20. The method of claim 19, wherein the subject is in need of a treatment of Alzheimer's Disease.

* * * * *

SEQUENCE LISTING

<160> NUMBER OF SEQ ID NOS: 45

<210> SEQ ID NO 1
<211> LENGTH: 21
<212> TYPE: PRT
<213> ORGANISM: Artificial Sequence
<220> FEATURE:
<223> OTHER INFORMATION: phospho-tau peptide 7.1
<220> FEATURE:
<221> NAME/KEY: phosphorylated serine
<222> LOCATION: (8)..(8)
<220> FEATURE:
<221> NAME/KEY: phosphorylated serine
<222> LOCATION: (11)..(11)
<220> FEATURE:
<221> NAME/KEY: phosphorylated threonine
<222> LOCATION: (14)..(14)

<400> SEQUENCE: 1

Gly Asp Arg Ser Gly Tyr Ser Ser Pro Gly Ser Pro Gly Thr Pro Gly
1               5                   10                  15

Ser Arg Ser Arg Thr
            20

<210> SEQ ID NO 2
<211> LENGTH: 16
<212> TYPE: PRT
<213> ORGANISM: Artificial Sequence
<220> FEATURE:
<223> OTHER INFORMATION: phospho-tau peptide T3.5
<220> FEATURE:
<221> NAME/KEY: phosphorylated serine
<222> LOCATION: (4)..(4)
<220> FEATURE:
<221> NAME/KEY: phosphorylated serine
<222> LOCATION: (12)..(12)

<400> SEQUENCE: 2

Val Tyr Lys Ser Pro Val Val Ser Gly Asp Thr Ser Pro Arg His Leu
1               5                   10                  15

```
<210> SEQ ID NO 3
<211> LENGTH: 18
<212> TYPE: PRT
<213> ORGANISM: Artificial Sequence
<220> FEATURE:
<223> OTHER INFORMATION: phospho-tau peptide 22.1
<220> FEATURE:
<221> NAME/KEY: phosphorylated serine
<222> LOCATION: (11)..(11)
<220> FEATURE:
<221> NAME/KEY: phosphorylated threonine
<222> LOCATION: (16)..(16)

<400> SEQUENCE: 3

Ser Ser Thr Gly Ser Ile Asp Met Val Asp Ser Pro Gln Leu Ala Thr
1               5                   10                  15

Leu Ala

<210> SEQ ID NO 4
<211> LENGTH: 16
<212> TYPE: PRT
<213> ORGANISM: Artificial Sequence
<220> FEATURE:
<223> OTHER INFORMATION: tau peptide

<400> SEQUENCE: 4

Val Tyr Lys Ser Pro Val Val Ser Gly Asp Thr Ser Pro Arg His Leu
1               5                   10                  15

<210> SEQ ID NO 5
<211> LENGTH: 30
<212> TYPE: PRT
<213> ORGANISM: Artificial Sequence
<220> FEATURE:
<223> OTHER INFORMATION: phospho-tau peptide
<220> FEATURE:
<221> NAME/KEY: phosphorylated serine
<222> LOCATION: (18)..(18)
<220> FEATURE:
<221> NAME/KEY: phosphorylated serine
<222> LOCATION: (26)..(26)

<400> SEQUENCE: 5

Arg Glu Asn Ala Lys Ala Lys Thr Asp His Gly Ala Glu Ile Val Tyr
1               5                   10                  15

Lys Ser Pro Val Val Ser Gly Asp Thr Ser Pro Arg His Leu
            20                  25                  30

<210> SEQ ID NO 6
<211> LENGTH: 16
<212> TYPE: PRT
<213> ORGANISM: Artificial Sequence
<220> FEATURE:
<223> OTHER INFORMATION: phospho-tau peptide
<220> FEATURE:
<221> NAME/KEY: phosphorylated tyrosine
<222> LOCATION: (14)..(14)

<400> SEQUENCE: 6

Arg Gln Glu Phe Glu Val Met Glu Asp His Ala Gly Thr Tyr Gly Leu
1               5                   10                  15

<210> SEQ ID NO 7
<211> LENGTH: 16
<212> TYPE: PRT
<213> ORGANISM: Artificial Sequence
<220> FEATURE:
```

```
<223> OTHER INFORMATION: phospho-tau peptide
<220> FEATURE:
<221> NAME/KEY: phosphorylated threonine
<222> LOCATION: (7)..(7)
<220> FEATURE:
<221> NAME/KEY: phosphorylated serine
<222> LOCATION: (9)..(9)

<400> SEQUENCE: 7

Pro Gly Ser Arg Ser Arg Thr Pro Ser Leu Pro Thr Pro Pro Thr Arg
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: phospho-tau peptide
<220> FEATURE:
<221> NAME/KEY: phosphorylated serine
<222> LOCATION: (7)..(7)
<220> FEATURE:
<221> NAME/KEY: phosphorylated threonine
<222> LOCATION: (10)..(10)

<400> SEQUENCE: 8

Gly Tyr Ser Ser Pro Gly Ser Pro Gly Thr Pro Gly Ser Arg Ser Arg
1               5                   10                  15

<210> SEQ ID NO 9
<211> LENGTH: 18
<212> TYPE: PRT
<213> ORGANISM: Artificial Sequence
<220> FEATURE:
<223> OTHER INFORMATION: phospho-tau peptide
<220> FEATURE:
<221> NAME/KEY: phosphorylated serine
<222> LOCATION: (4)..(4)
<220> FEATURE:
<221> NAME/KEY: phosphorylated serine
<222> LOCATION: (9)..(9)

<400> SEQUENCE: 9

Gly Asp Thr Ser Pro Arg His Leu Ser Asn Val Ser Ser Thr Gly Ser
1               5                   10                  15

Ile Asp

<210> SEQ ID NO 10
<211> LENGTH: 17
<212> TYPE: PRT
<213> ORGANISM: Artificial Sequence
<220> FEATURE:
<223> OTHER INFORMATION: phospho-tau peptide
<220> FEATURE:
<221> NAME/KEY: phosphorylated serine
<222> LOCATION: (3)..(3)
<220> FEATURE:
<221> NAME/KEY: phosphorylated threonine
<222> LOCATION: (6)..(6)
<220> FEATURE:
<221> NAME/KEY: phosphorylated threonine
<222> LOCATION: (13)..(13)
<220> FEATURE:
<221> NAME/KEY: phosphorylated serine
<222> LOCATION: (15)..(15)

<400> SEQUENCE: 10

Pro Gly Ser Pro Gly Thr Pro Gly Ser Arg Ser Arg Thr Pro Ser Leu
1               5                   10                  15

Pro
```

```
<210> SEQ ID NO 11
<211> LENGTH: 12
<212> TYPE: PRT
<213> ORGANISM: Artificial Sequence
<220> FEATURE:
<223> OTHER INFORMATION: phospho-tau peptide
<220> FEATURE:
<221> NAME/KEY: phosphorylated serine
<222> LOCATION: (3)..(3)

<400> SEQUENCE: 11

His Leu Ser Asn Val Ser Ser Thr Gly Ser Ile Asp
1               5                   10

<210> SEQ ID NO 12
<211> LENGTH: 10
<212> TYPE: PRT
<213> ORGANISM: Artificial Sequence
<220> FEATURE:
<223> OTHER INFORMATION: phospho-tau peptide
<220> FEATURE:
<221> NAME/KEY: phosphorylated serine
<222> LOCATION: (6)..(6)

<400> SEQUENCE: 12

Val Ser Gly Asp Thr Ser Pro Arg His Leu
1               5                   10

<210> SEQ ID NO 13
<211> LENGTH: 55
<212> TYPE: PRT
<213> ORGANISM: Artificial Sequence
<220> FEATURE:
<223> OTHER INFORMATION: T50 T cell epitope
<220> FEATURE:
<221> NAME/KEY: C-terminal amide
<222> LOCATION: (55)..(55)

<400> SEQUENCE: 13

Ala Lys Phe Val Ala Ala Trp Thr Leu Lys Ala Ala Ala Val Val Arg
1               5                   10                  15

Gln Tyr Ile Lys Ala Asn Ser Lys Phe Ile Gly Ile Thr Glu Leu Val
            20                  25                  30

Val Arg Phe Asn Asn Phe Thr Val Ser Phe Trp Leu Arg Val Pro Lys
        35                  40                  45

Val Ser Ala Ser His Leu Glu
        50                  55

<210> SEQ ID NO 14
<211> LENGTH: 55
<212> TYPE: PRT
<213> ORGANISM: Artificial Sequence
<220> FEATURE:
<223> OTHER INFORMATION: T46 T cell epitope
<220> FEATURE:
<221> NAME/KEY: palmitoylated lysine
<222> LOCATION: (54)..(54)
<220> FEATURE:
<221> NAME/KEY: palmitoylated lysine
<222> LOCATION: (55)..(55)
<220> FEATURE:
<221> NAME/KEY: C-terminal amide
<222> LOCATION: (55)..(55)

<400> SEQUENCE: 14

Ala Lys Phe Val Ala Ala Trp Thr Leu Lys Ala Ala Ala Gly Ser Gln
1               5                   10                  15
```

```
Tyr Ile Lys Ala Asn Ser Lys Phe Ile Gly Ile Thr Glu Leu Gly Ser
            20                  25                  30

Phe Asn Asn Phe Thr Val Ser Phe Trp Leu Arg Val Pro Lys Val Ser
        35                  40                  45

Ala Ser His Leu Glu Lys Lys
    50                  55

<210> SEQ ID NO 15
<211> LENGTH: 75
<212> TYPE: PRT
<213> ORGANISM: Artificial Sequence
<220> FEATURE:
<223> OTHER INFORMATION: T48 helper T cell epitope
<220> FEATURE:
<221> NAME/KEY: C-terminal amide
<222> LOCATION: (75)..(75)

<400> SEQUENCE: 15

Ala Lys Phe Val Ala Ala Trp Thr Leu Lys Ala Ala Gly Ser Gln
1               5                   10                  15

Tyr Ile Lys Ala Asn Ser Lys Phe Ile Gly Ile Thr Glu Leu Gly Ser
            20                  25                  30

Phe Asn Asn Phe Thr Val Ser Phe Trp Leu Arg Val Pro Lys Val Ser
        35                  40                  45

Ala Ser His Leu Glu Gly Ser Leu Ile Asn Ser Thr Lys Ile Tyr Ser
    50                  55                  60

Tyr Phe Pro Ser Val Ile Ser Lys Val Asn Gln
65                  70                  75

<210> SEQ ID NO 16
<211> LENGTH: 53
<212> TYPE: PRT
<213> ORGANISM: Artificial Sequence
<220> FEATURE:
<223> OTHER INFORMATION: T51 helper T cell epitope
<220> FEATURE:
<221> NAME/KEY: C-terminal amide
<222> LOCATION: (53)..(53)

<400> SEQUENCE: 16

Ala Lys Phe Val Ala Ala Trp Thr Leu Lys Ala Ala Arg Arg Gln
1               5                   10                  15

Tyr Ile Lys Ala Asn Ser Lys Phe Ile Gly Ile Thr Glu Leu Arg Arg
            20                  25                  30

Phe Asn Asn Phe Thr Val Ser Phe Trp Leu Arg Val Pro Lys Val Ser
        35                  40                  45

Ala Ser His Leu Glu
    50

<210> SEQ ID NO 17
<211> LENGTH: 53
<212> TYPE: PRT
<213> ORGANISM: Artificial Sequence
<220> FEATURE:
<223> OTHER INFORMATION: T52 helper T cell epitope
<220> FEATURE:
<221> NAME/KEY: C-terminal amide
<222> LOCATION: (53)..(53)

<400> SEQUENCE: 17

Ala Lys Phe Val Ala Ala Trp Thr Leu Lys Ala Ala Arg Lys Gln
1               5                   10                  15
```

```
Tyr Ile Lys Ala Asn Ser Lys Phe Ile Gly Ile Thr Glu Leu Arg Lys
                20                  25                  30

Phe Asn Asn Phe Thr Val Ser Phe Trp Leu Arg Val Pro Lys Val Ser
        35                  40                  45

Ala Ser His Leu Glu
    50

<210> SEQ ID NO 18
<211> LENGTH: 24
<212> TYPE: DNA
<213> ORGANISM: Artificial Sequence
<220> FEATURE:
<223> OTHER INFORMATION: CpG 2006
<220> FEATURE:
<221> NAME/KEY: phosphorothioate (ps) internucleotide linkages
<222> LOCATION: (1)..(24)

<400> SEQUENCE: 18
tcgtcgtttt gtcgttttgt cgtt                                          24

<210> SEQ ID NO 19
<211> LENGTH: 22
<212> TYPE: DNA
<213> ORGANISM: Artificial Sequence
<220> FEATURE:
<223> OTHER INFORMATION: CpG 1018
<220> FEATURE:
<221> NAME/KEY: phosphorothioate (ps) internucleotide linkages
<222> LOCATION: (1)..(22)

<400> SEQUENCE: 19
tgactgtgaa cgttcgagat ga                                            22

<210> SEQ ID NO 20
<211> LENGTH: 22
<212> TYPE: DNA
<213> ORGANISM: Artificial Sequence
<220> FEATURE:
<223> OTHER INFORMATION: CpG 2395
<220> FEATURE:
<221> NAME/KEY: phosphorothioate (ps) internucleotide linkages
<222> LOCATION: (1)..(22)

<400> SEQUENCE: 20
tcgtcgtttt cggcgcgcgc cg                                            22

<210> SEQ ID NO 21
<211> LENGTH: 20
<212> TYPE: DNA
<213> ORGANISM: Artificial Sequence
<220> FEATURE:
<223> OTHER INFORMATION: CpG 2216
<220> FEATURE:
<221> NAME/KEY: phosphorothioate (ps) internucleotide linkages
<222> LOCATION: (1)..(3)
<220> FEATURE:
<221> NAME/KEY: phosphodiester (po) internucleotide linkages
<222> LOCATION: (3)..(14)
<220> FEATURE:
<221> NAME/KEY: phosphorothioate (ps) internucleotide linkages
<222> LOCATION: (14)..(20)

<400> SEQUENCE: 21
gggggacgat cgtcggggggg                                              20

<210> SEQ ID NO 22
<211> LENGTH: 21
<212> TYPE: DNA
```

```
<213> ORGANISM: Artificial Sequence
<220> FEATURE:
<223> OTHER INFORMATION: CpG 2336
<220> FEATURE:
<221> NAME/KEY: phosphorothioate (ps) internucleotide linkages
<222> LOCATION: (1)..(4)
<220> FEATURE:
<221> NAME/KEY: phosphodiester (po) internucleotide linkages
<222> LOCATION: (4)..(15)
<220> FEATURE:
<221> NAME/KEY: phosphorothioate (ps) internucleotide linkages
<222> LOCATION: (15)..(21)

<400> SEQUENCE: 22
ggggacgacg tcgtgggggg g                                              21

<210> SEQ ID NO 23
<211> LENGTH: 13
<212> TYPE: PRT
<213> ORGANISM: Artificial Sequence
<220> FEATURE:
<223> OTHER INFORMATION: Pan DR epitope (PADRE) peptide

<400> SEQUENCE: 23

Ala Lys Phe Val Ala Ala Trp Thr Leu Lys Ala Ala Ala
1               5                   10

<210> SEQ ID NO 24
<211> LENGTH: 15
<212> TYPE: PRT
<213> ORGANISM: Artificial Sequence
<220> FEATURE:
<223> OTHER INFORMATION: P2

<400> SEQUENCE: 24

Gln Tyr Ile Lys Ala Asn Ser Lys Phe Ile Gly Ile Thr Glu Leu
1               5                   10                  15

<210> SEQ ID NO 25
<211> LENGTH: 21
<212> TYPE: PRT
<213> ORGANISM: Artificial Sequence
<220> FEATURE:
<223> OTHER INFORMATION: P30

<400> SEQUENCE: 25

Phe Asn Asn Phe Thr Val Ser Phe Trp Leu Arg Val Pro Lys Val Ser
1               5                   10                  15

Ala Ser His Leu Glu
            20

<210> SEQ ID NO 26
<211> LENGTH: 20
<212> TYPE: PRT
<213> ORGANISM: Artificial Sequence
<220> FEATURE:
<223> OTHER INFORMATION: TT586-605

<400> SEQUENCE: 26

Leu Ile Asn Ser Thr Lys Ile Tyr Ser Tyr Phe Pro Ser Val Ile Ser
1               5                   10                  15

Lys Val Asn Gln
            20

<210> SEQ ID NO 27
<211> LENGTH: 25
<212> TYPE: PRT
```

-continued

```
<213> ORGANISM: Artificial Sequence
<220> FEATURE:
<223> OTHER INFORMATION: palmitoylated phospho-tau peptide
      (palmitoylated 7.1)
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated serine
<222> LOCATION: (10)..(10)
<220> FEATURE:
<221> NAME/KEY: phosphorylated serine
<222> LOCATION: (13)..(13)
<220> FEATURE:
<221> NAME/KEY: phosphorylated threonine
<222> LOCATION: (16)..(16)
<220> FEATURE:
<221> NAME/KEY: palmitoylated lysine
<222> LOCATION: (24)..(24)
<220> FEATURE:
<221> NAME/KEY: palmitoylated lysine
<222> LOCATION: (25)..(25)

<400> SEQUENCE: 27

Lys Lys Gly Asp Arg Ser Gly Tyr Ser Ser Pro Gly Ser Pro Gly Thr
1               5                   10                  15

Pro Gly Ser Arg Ser Arg Thr Lys Lys
            20                  25

<210> SEQ ID NO 28
<211> LENGTH: 20
<212> TYPE: PRT
<213> ORGANISM: Artificial Sequence
<220> FEATURE:
<223> OTHER INFORMATION: palmitoylated phospho-tau peptide (T3,
      palmitoylated T3.5)
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated serine
<222> LOCATION: (6)..(6)
<220> FEATURE:
<221> NAME/KEY: phosphorylated serine
<222> LOCATION: (14)..(14)
<220> FEATURE:
<221> NAME/KEY: palmitoylated lysine
<222> LOCATION: (19)..(19)
<220> FEATURE:
<221> NAME/KEY: palmitoylated lysine
<222> LOCATION: (20)..(20)

<400> SEQUENCE: 28

Lys Lys Val Tyr Lys Ser Pro Val Val Ser Gly Asp Thr Ser Pro Arg
1               5                   10                  15

His Leu Lys Lys
            20

<210> SEQ ID NO 29
<211> LENGTH: 22
<212> TYPE: PRT
<213> ORGANISM: Artificial Sequence
<220> FEATURE:
<223> OTHER INFORMATION: palmitoylated phospho-tau peptide
      (palmitoylated 22.1)
<220> FEATURE:
<221> NAME/KEY: palmitoylated lysine
```

```
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated serine
<222> LOCATION: (13)..(13)
<220> FEATURE:
<221> NAME/KEY: phosphorylated threonine
<222> LOCATION: (18)..(18)
<220> FEATURE:
<221> NAME/KEY: palmitoylated lysine
<222> LOCATION: (21)..(21)
<220> FEATURE:
<221> NAME/KEY: palmitoylated lysine
<222> LOCATION: (22)..(22)

<400> SEQUENCE: 29

Lys Lys Ser Ser Thr Gly Ser Ile Asp Met Val Asp Ser Pro Gln Leu
1               5                   10                  15

Ala Thr Leu Ala Lys Lys
            20

<210> SEQ ID NO 30
<211> LENGTH: 20
<212> TYPE: PRT
<213> ORGANISM: Artificial Sequence
<220> FEATURE:
<223> OTHER INFORMATION: palmitoylated tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: palmitoylated lysine
<222> LOCATION: (19)..(19)
<220> FEATURE:
<221> NAME/KEY: palmitoylated lysine
<222> LOCATION: (20)..(20)

<400> SEQUENCE: 30

Lys Lys Val Tyr Lys Ser Pro Val Val Ser Gly Asp Thr Ser Pro Arg
1               5                   10                  15

His Leu Lys Lys
            20

<210> SEQ ID NO 31
<211> LENGTH: 34
<212> TYPE: PRT
<213> ORGANISM: Artificial Sequence
<220> FEATURE:
<223> OTHER INFORMATION: palmitoylated phospho-tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated serine
<222> LOCATION: (20)..(20)
<220> FEATURE:
<221> NAME/KEY: phosphorylated serine
<222> LOCATION: (28)..(28)
<220> FEATURE:
<221> NAME/KEY: palmitoylated lysine
<222> LOCATION: (33)..(33)
<220> FEATURE:
<221> NAME/KEY: palmitoylated lysine
<222> LOCATION: (34)..(34)
```

```
<400> SEQUENCE: 31

Lys Lys Arg Glu Asn Ala Lys Ala Lys Thr Asp His Gly Ala Glu Ile
1               5                   10                  15

Val Tyr Lys Ser Pro Val Val Ser Gly Asp Thr Ser Pro Arg His Leu
                20                  25                  30

Lys Lys

<210> SEQ ID NO 32
<211> LENGTH: 20
<212> TYPE: PRT
<213> ORGANISM: Artificial Sequence
<220> FEATURE:
<223> OTHER INFORMATION: palmitoylated phospho-tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated tyrosine
<222> LOCATION: (16)..(16)
<220> FEATURE:
<221> NAME/KEY: palmitoylated lysine
<222> LOCATION: (19)..(19)
<220> FEATURE:
<221> NAME/KEY: palmitoylated lysine
<222> LOCATION: (20)..(20)

<400> SEQUENCE: 32

Lys Lys Arg Gln Glu Phe Glu Val Met Glu Asp His Ala Gly Thr Tyr
1               5                   10                  15

Gly Leu Lys Lys
                20

<210> SEQ ID NO 33
<211> LENGTH: 20
<212> TYPE: PRT
<213> ORGANISM: Artificial Sequence
<220> FEATURE:
<223> OTHER INFORMATION: palmitoylated phospho-tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated threonine
<222> LOCATION: (9)..(9)
<220> FEATURE:
<221> NAME/KEY: phosphorylated serine
<222> LOCATION: (11)..(11)
<220> FEATURE:
<221> NAME/KEY: palmitoylated lysine
<222> LOCATION: (19)..(19)
<220> FEATURE:
<221> NAME/KEY: palmitoylated lysine
<222> LOCATION: (20)..(20)

<400> SEQUENCE: 33

Lys Lys Pro Gly Ser Arg Ser Arg Thr Pro Ser Leu Pro Thr Pro Pro
1               5                   10                  15

Thr Arg Lys Lys
                20

<210> SEQ ID NO 34
<211> LENGTH: 20
<212> TYPE: PRT
```

<213> ORGANISM: Artificial Sequence
<220> FEATURE:
<223> OTHER INFORMATION: palmitoylated phospho-tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated serine
<222> LOCATION: (9)..(9)
<220> FEATURE:
<221> NAME/KEY: phosphorylated threonine
<222> LOCATION: (12)..(12)
<220> FEATURE:
<221> NAME/KEY: palmitoylated lysine
<222> LOCATION: (19)..(19)
<220> FEATURE:
<221> NAME/KEY: palmitoylated lysine
<222> LOCATION: (20)..(20)

<400> SEQUENCE: 34

Lys Lys Gly Tyr Ser Ser Pro Gly Ser Pro Gly Thr Pro Gly Ser Arg
1               5                   10                  15

Ser Arg Lys Lys
            20

<210> SEQ ID NO 35
<211> LENGTH: 22
<212> TYPE: PRT
<213> ORGANISM: Artificial Sequence
<220> FEATURE:
<223> OTHER INFORMATION: palmitoylated phospho-tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated serine
<222> LOCATION: (6)..(6)
<220> FEATURE:
<221> NAME/KEY: phosphorylated serine
<222> LOCATION: (11)..(11)
<220> FEATURE:
<221> NAME/KEY: palmitoylated lysine
<222> LOCATION: (21)..(21)
<220> FEATURE:
<221> NAME/KEY: palmitoylated lysine
<222> LOCATION: (22)..(22)

<400> SEQUENCE: 35

Lys Lys Gly Asp Thr Ser Pro Arg His Leu Ser Asn Val Ser Ser Thr
1               5                   10                  15

Gly Ser Ile Asp Lys Lys
            20

<210> SEQ ID NO 36
<211> LENGTH: 21
<212> TYPE: PRT
<213> ORGANISM: Artificial Sequence
<220> FEATURE:
<223> OTHER INFORMATION: palmitoylated phospho-tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated serine

```
<222> LOCATION: (5)..(5)
<220> FEATURE:
<221> NAME/KEY: phosphorylated threonine
<222> LOCATION: (8)..(8)
<220> FEATURE:
<221> NAME/KEY: phosphorylated threonine
<222> LOCATION: (15)..(15)
<220> FEATURE:
<221> NAME/KEY: phosphorylated serine
<222> LOCATION: (17)..(17)
<220> FEATURE:
<221> NAME/KEY: palmitoylated lysine
<222> LOCATION: (20)..(20)
<220> FEATURE:
<221> NAME/KEY: palmitoylated lysine
<222> LOCATION: (21)..(21)

<400> SEQUENCE: 36

Lys Lys Pro Gly Ser Pro Gly Thr Pro Gly Ser Arg Ser Arg Thr Pro
1               5                   10                  15

Ser Leu Pro Lys Lys
            20

<210> SEQ ID NO 37
<211> LENGTH: 16
<212> TYPE: PRT
<213> ORGANISM: Artificial Sequence
<220> FEATURE:
<223> OTHER INFORMATION: palmitoylated phospho-tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated serine
<222> LOCATION: (5)..(5)
<220> FEATURE:
<221> NAME/KEY: palmitoylated lysine
<222> LOCATION: (15)..(15)
<220> FEATURE:
<221> NAME/KEY: palmitoylated lysine
<222> LOCATION: (16)..(16)

<400> SEQUENCE: 37

Lys Lys His Leu Ser Asn Val Ser Ser Thr Gly Ser Ile Asp Lys Lys
1               5                   10                  15

<210> SEQ ID NO 38
<211> LENGTH: 14
<212> TYPE: PRT
<213> ORGANISM: Artificial Sequence
<220> FEATURE:
<223> OTHER INFORMATION: palmitoylated phospho-tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated serine
<222> LOCATION: (8)..(8)
<220> FEATURE:
<221> NAME/KEY: palmitoylated lysine
<222> LOCATION: (13)..(13)
<220> FEATURE:
<221> NAME/KEY: palmitoylated lysine
<222> LOCATION: (14)..(14)

<400> SEQUENCE: 38

Lys Lys Val Ser Gly Asp Thr Ser Pro Arg His Leu Lys Lys
```

```
                1               5                    10
```

<210> SEQ ID NO 39
<211> LENGTH: 55
<212> TYPE: PRT
<213> ORGANISM: Artificial Sequence
<220> FEATURE:
<223> OTHER INFORMATION: T50 without the C-terminal amide

<400> SEQUENCE: 39

```
Ala Lys Phe Val Ala Ala Trp Thr Leu Lys Ala Ala Ala Val Val Arg
1               5                   10                  15

Gln Tyr Ile Lys Ala Asn Ser Lys Phe Ile Gly Ile Thr Glu Leu Val
            20                  25                  30

Val Arg Phe Asn Asn Phe Thr Val Ser Phe Trp Leu Arg Val Pro Lys
        35                  40                  45

Val Ser Ala Ser His Leu Glu
    50                  55
```

<210> SEQ ID NO 40
<211> LENGTH: 53
<212> TYPE: PRT
<213> ORGANISM: Artificial Sequence
<220> FEATURE:
<223> OTHER INFORMATION: T46 without the palmitoylated lysines and
      C-terminal amide

<400> SEQUENCE: 40

```
Ala Lys Phe Val Ala Ala Trp Thr Leu Lys Ala Ala Ala Gly Ser Gln
1               5                   10                  15

Tyr Ile Lys Ala Asn Ser Lys Phe Ile Gly Ile Thr Glu Leu Gly Ser
            20                  25                  30

Phe Asn Asn Phe Thr Val Ser Phe Trp Leu Arg Val Pro Lys Val Ser
        35                  40                  45

Ala Ser His Leu Glu
    50
```

<210> SEQ ID NO 41
<211> LENGTH: 75
<212> TYPE: PRT
<213> ORGANISM: Artificial Sequence
<220> FEATURE:
<223> OTHER INFORMATION: T48 without the C-terminal amide

<400> SEQUENCE: 41

```
Ala Lys Phe Val Ala Ala Trp Thr Leu Lys Ala Ala Ala Gly Ser Gln
1               5                   10                  15

Tyr Ile Lys Ala Asn Ser Lys Phe Ile Gly Ile Thr Glu Leu Gly Ser
            20                  25                  30

Phe Asn Asn Phe Thr Val Ser Phe Trp Leu Arg Val Pro Lys Val Ser
        35                  40                  45

Ala Ser His Leu Glu Gly Ser Leu Ile Asn Ser Thr Lys Ile Tyr Ser
    50                  55                  60

Tyr Phe Pro Ser Val Ile Ser Lys Val Asn Gln
65                  70                  75
```

<210> SEQ ID NO 42
<211> LENGTH: 53
<212> TYPE: PRT
<213> ORGANISM: Artificial Sequence
<220> FEATURE:
<223> OTHER INFORMATION: T51 without the C-terminal amide -continued

```
<400> SEQUENCE: 42

Ala Lys Phe Val Ala Ala Trp Thr Leu Lys Ala Ala Arg Arg Gln
1               5                   10                  15

Tyr Ile Lys Ala Asn Ser Lys Phe Ile Gly Ile Thr Glu Leu Arg Arg
            20                  25                  30

Phe Asn Asn Phe Thr Val Ser Phe Trp Leu Arg Val Pro Lys Val Ser
        35                  40                  45

Ala Ser His Leu Glu
    50

<210> SEQ ID NO 43
<211> LENGTH: 53
<212> TYPE: PRT
<213> ORGANISM: Artificial Sequence
<220> FEATURE:
<223> OTHER INFORMATION: T52 without the C-terminal amide

<400> SEQUENCE: 43

Ala Lys Phe Val Ala Ala Trp Thr Leu Lys Ala Ala Arg Lys Gln
1               5                   10                  15

Tyr Ile Lys Ala Asn Ser Lys Phe Ile Gly Ile Thr Glu Leu Arg Lys
            20                  25                  30

Phe Asn Asn Phe Thr Val Ser Phe Trp Leu Arg Val Pro Lys Val Ser
        35                  40                  45

Ala Ser His Leu Glu
    50

<210> SEQ ID NO 44
<211> LENGTH: 57
<212> TYPE: PRT
<213> ORGANISM: Artificial Sequence
<220> FEATURE:
<223> OTHER INFORMATION: T57
<220> FEATURE:
<221> NAME/KEY: palmitoylated lysine
<222> LOCATION: (56)..(56)
<220> FEATURE:
<221> NAME/KEY: palmitoylated lysine
<222> LOCATION: (57)..(57)
<220> FEATURE:
<221> NAME/KEY: C-terminal amide
<222> LOCATION: (57)..(57)

<400> SEQUENCE: 44

Ala Lys Phe Val Ala Ala Trp Thr Leu Lys Ala Ala Val Val Arg
1               5                   10                  15

Gln Tyr Ile Lys Ala Asn Ser Lys Phe Ile Gly Ile Thr Glu Leu Val
            20                  25                  30

Val Arg Phe Asn Asn Phe Thr Val Ser Phe Trp Leu Arg Val Pro Lys
        35                  40                  45

Val Ser Ala Ser His Leu Glu Lys Lys
    50                  55

<210> SEQ ID NO 45
<211> LENGTH: 13
<212> TYPE: PRT
```

```
<213> ORGANISM: Artificial Sequence
<220> FEATURE:
<223> OTHER INFORMATION: synthetic peptide derived from amino acids 294
      to 305 of the Tau sequence

<400> SEQUENCE: 45

Cys Lys Asp Asn Ile Lys His Val Pro Gly Gly Gly Ser
1               5                   10
```